United States Patent [19]
Cohen et al.

[11] Patent Number: 6,096,314
[45] Date of Patent: Aug. 1, 2000

[54] PEPTIDES AND PHARMACEUTICAL COMPOSITIONS COMPRISING THEM

[75] Inventors: Irun R. Cohen; Dana Elias, both of Rehovot, Israel

[73] Assignee: Yeda Research and Development Co. Ltd., Rehovot, Israel

[21] Appl. No.: 08/817,177

[22] PCT Filed: Oct. 10, 1995

[86] PCT No.: PCT/US95/12686

§ 371 Date: Jun. 20, 1997

§ 102(e) Date: Jun. 20, 1997

[87] PCT Pub. No.: WO96/11214

PCT Pub. Date: Apr. 18, 1996

[30] Foreign Application Priority Data

Oct. 7, 1994 [IL] Israel ......................................... 111196

[51] Int. Cl.⁷ .......................... A61K 39/00; C07K 14/725
[52] U.S. Cl. ..................... 424/185.1; 424/193.1; 435/7.24; 435/69.3; 530/300; 530/395; 530/403; 536/23.5
[58] Field of Search .................. 424/185.1; 530/350, 530/395, 328

[56] References Cited

U.S. PATENT DOCUMENTS

| | | | |
|---|---|---|---|
| 5,578,303 | 11/1996 | Cohen | 424/93.71 |
| 5,612,035 | 3/1997 | Howell et al. | 424/185.1 |
| 5,614,192 | 3/1997 | Vandenbark | 424/185.1 |

OTHER PUBLICATIONS

Smilek, D. et al., PNAS 88:9633–9637, A single amino acid change in a myelin basic protein peptide confers the capacity to prevent rather than induce experimental autoimmun encephalomyelitis, Nov. 1991.

Bona, C. et al., Immunology Today 19(3):126–133, Towards development of T–cell vaccines, Mar. 1998.

D. Elias et al., "Induction and therapy of autoimmune diabetes in the non–obese–diabetic (NOD/Lt) mouse by a 65–kDa heat shock protein", Proc. Natl. Acad. Sci. USA, vol. 87, pp. 1576–1580, Feb. 1990.

D. Elias et al., "Vaccination against autoimmune mouse diabetes with a T–cell epitope of the human 65–kDa heat shock protein", Proc. Natl. Sci. USA, vol. 88, pp. 3088–3091, Apr. 1991.

O. Lider et al., "Anti–idiotypic network induced by T cell vaccination against experimental autoimmune encephalomyelitis", Science, vol. 239, pp. 181–183, Jan. 8, 1988.

J. Zhang et al., "MHC–restricted depletion of human myelin basic protein–reactive T cells by T cell vaccination", Science, vol. 261, pp. 1451–1454, Sep. 10, 1993.

N. Nakano et al., "T cell receptor V gene usage of islet β cell–reactive T cells is not restricted in non–obese diabetic mice", J. Exp. Med., vol. 173, pp. 1091–1097, May 1991.

I. Durinovic–Bello et al., "HLA–DQ–restricted, islet–specific T cell clones of a Type I diabetic patient: T cell receptor sequence similarities to insulitis–inducing T cells of non-obese diabetic (NOD) mice", 13th International Immunology and Diabetes Workshop, p. 101, May 1994.

I. Durinovic–Bello et al., "HLA–DQ–restricted, islet–specific T–cell clones of a Type 1 diabetic patient: T–cell receptor sequence similarities to insulitis–inducing T–cells of nonobese diabetic Mice", Diabetes, vol. 43, pp. 1318–1325, Nov. 1994.

A. Bendelac et al., "Syngeneic transfer of autoimmune diabetes from diabetic NOD mice to healthy neonates: Requirement for both L3T4 and Lyt–2 T cells", J. Exp. Med., vol. 166, pp. 823–832, 1987.

M. Howell et al., "Vaccination against experimental allergic encephalomyelitis with T cell receptor peptides" Science, vol. 246, pp. 668–670, 1989.

A. Vandenbark et al., "Immunization with a synthetic T–cell receptor V–region peptide protects against experimental autoimmune encephalomyelitis", Nature, vol. 322, pp. 379–382, 1984.

U. McKeever et al., "Immunization with soluble BDC 2.5 T cell receptor–immunoglobulin chimeric protein: Antibody specificity and protection of nonobese diabetic mice against adoptive transfer of diabetes by maternal immunization", J. Exp. Med., vol. 184, pp. 1655–1768, Nov. 1996.

H. Naserke et al., "The T–cell receptor beta chain CDR3 region BV8S1/BJ1S5 transcripts in type 1 diabetes", Immunogenetics, vol. 45, pp. 87–96, 1996.

*Primary Examiner*—Thomas M. Cunningham
*Attorney, Agent, or Firm*—Browdy and Neimark

[57] ABSTRACT

The present invention relates generally to peptide sequences, and method of their use, which sequences modulate the activity of anti-idiotypic T cells. The activity of the anti-idiotypic T cells of interest is related to the ability of these T cells to recognize anti-p277 T cells. The peptides of the present invention thus include important tools in the effort to diagnose, prevent, alleviate or treat disease related to insulin-dependent diabetes mellitus (IDDM).

32 Claims, 8 Drawing Sheets

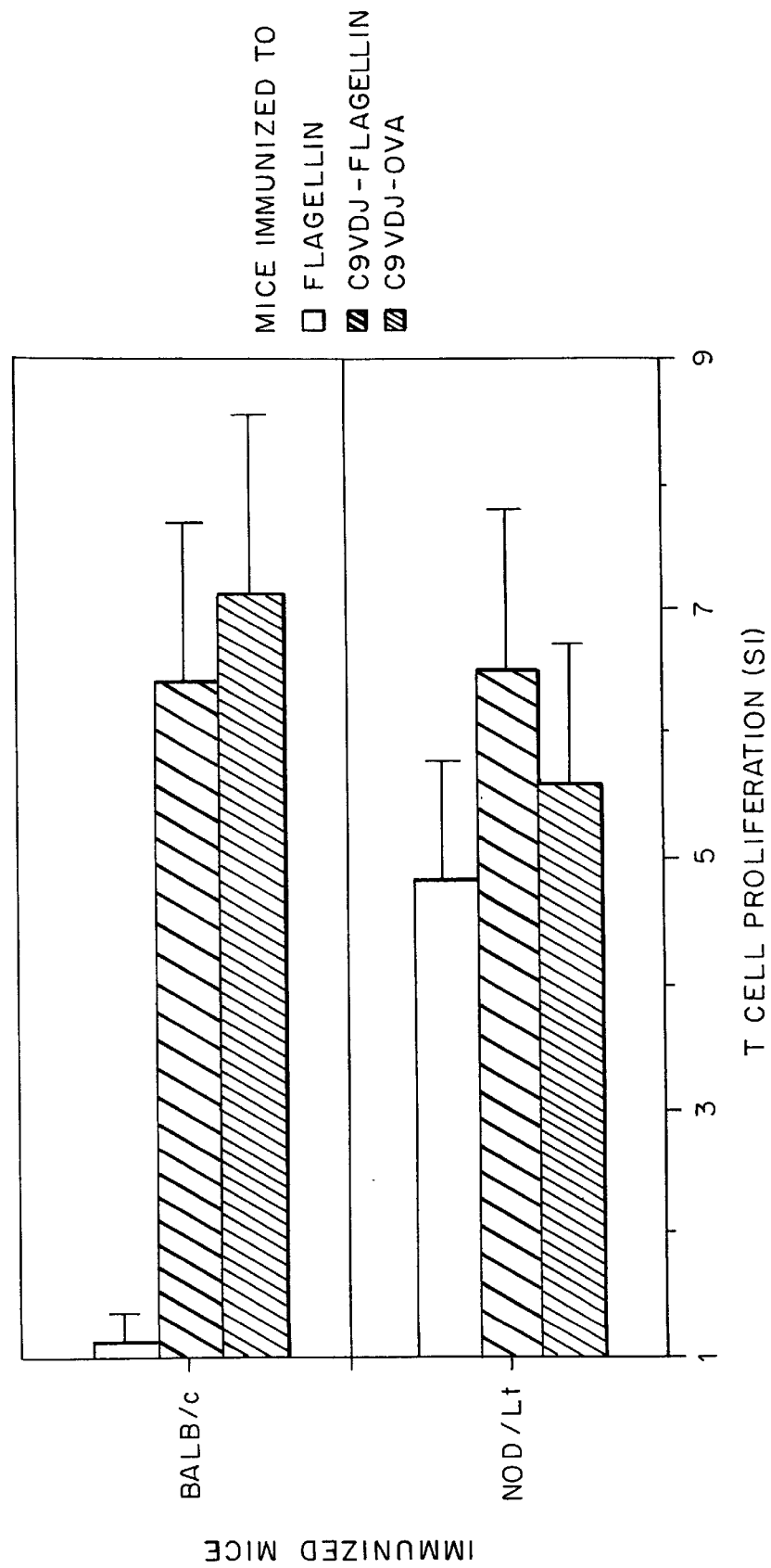

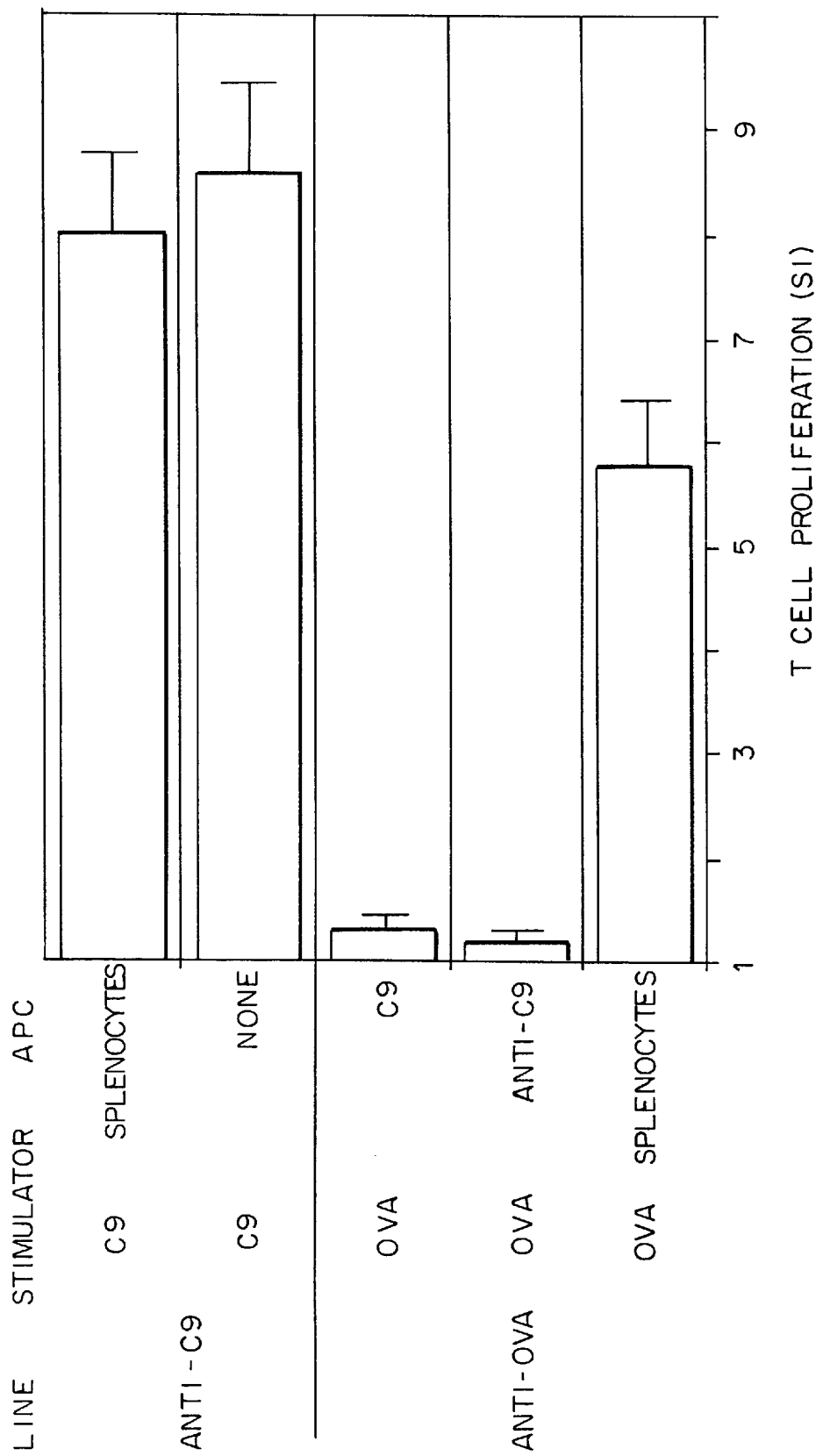

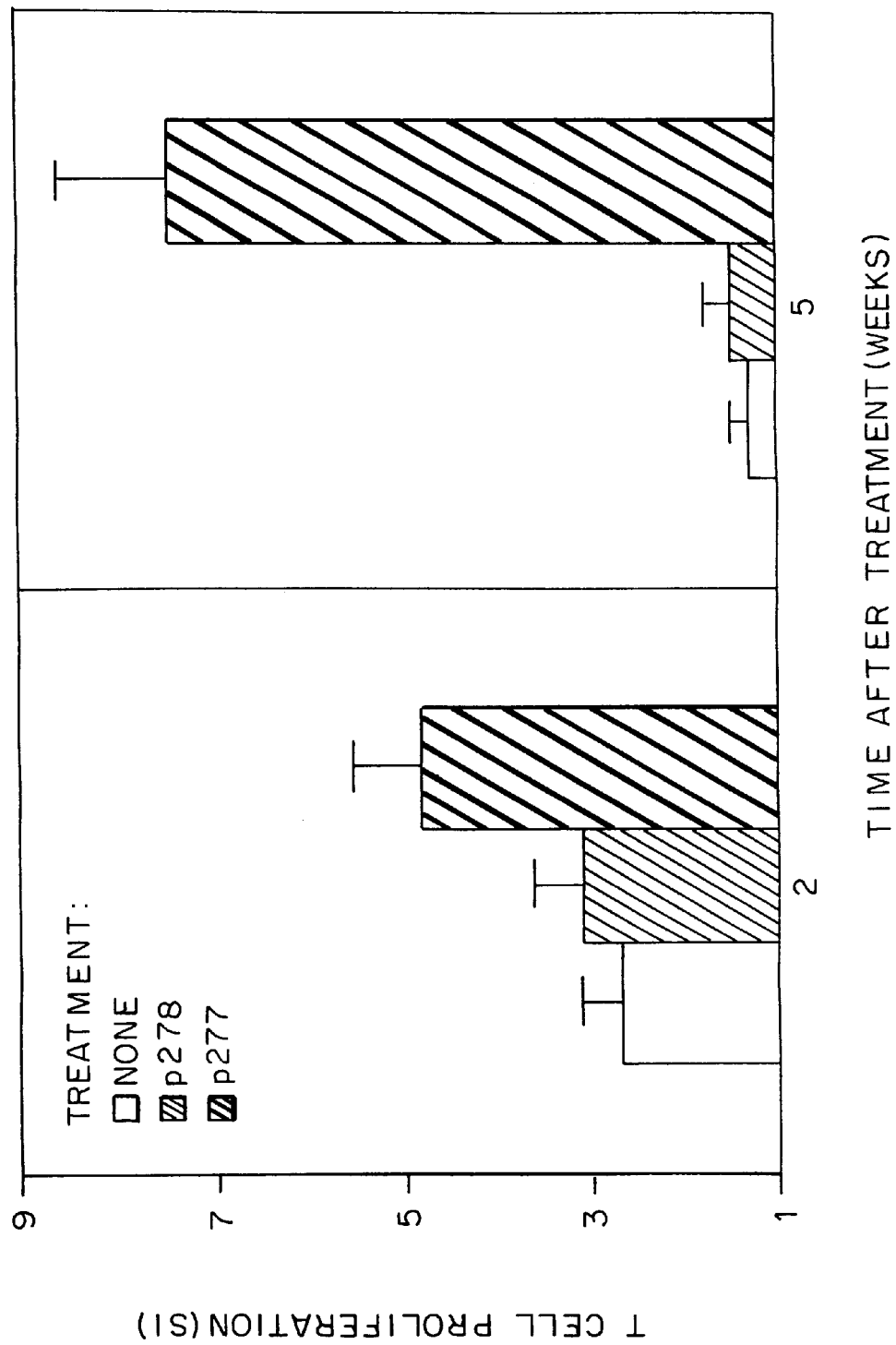

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Ser Tyr Phe Arg Ser Lys Ser Leu Met Glu Asp Gly Gly Ala Phe Lys
1               5                   10                  15

Asp Arg Phe Lys Ala Glu Asn Leu Asn Ser Ser Phe Ser Thr Leu Lys
                20                  25                  30

Leu Gln Pro Thr Glu Pro Lys Asp Ser Ala Val Tyr Leu Cys Ala Ser
            35                  40                  45

Ser Leu Gly Gly Asn Gln Asp Thr Gln Tyr Phe Gly Pro Gly Thr Arg
    50                  55                  60

Leu Leu Val Leu
65

(2) INFORMATION FOR SEQ ID NO: 2:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Ala Ser Ser Leu Trp Thr Asn Gln Asp Thr Gln Tyr
1               5                   10

```
(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Ala Ser Arg Leu Gly Asn Gln Asp
1               5

(2) INFORMATION FOR SEQ ID NO: 4:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Ala Ser Ser Leu Gly Leu Gly Ala Asn Gln Asp
1               5                   10

(2) INFORMATION FOR SEQ ID NO: 5:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Val Leu Gly Gly Gly Cys Ala Leu Leu Arg Cys Ile Pro Ala Leu Asp
1               5                   10                  15

Ser Leu Thr Pro Ala Asn Glu Asp
            20

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

GCCAGCAGTT TAGGGGGTAA CCAAGAC                                          27

(2) INFORMATION FOR SEQ ID NO: 7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO: 7:

Thr Gly Gly Cys Gly Thr Thr Gly Gly Thr Cys Thr Cys Thr Thr Thr
1               5                   10                  15

Gly Ala Ala Gly
            20

(2) INFORMATION FOR SEQ ID NO: 8:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 8:

CGGCACATTG ATTTGGGAGT C                                                             21

(2) INFORMATION FOR SEQ ID NO: 9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 9:

ACACAGCAGG TTCTGGGTTC                                                               20

(2) INFORMATION FOR SEQ ID NO: 10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 10:

ATGAGAGGGC CTAATTAC                                                                 18

(2) INFORMATION FOR SEQ ID NO: 11:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 11:

Met Arg Gly Pro Asn Trp
1               5

(2) INFORMATION FOR SEQ ID NO: 12:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 12:

Ser Arg Leu Gly Asn Gln Asp Thr Gln Tyr
1               5                   10

(2) INFORMATION FOR SEQ ID NO: 13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GCAAGAAGCT TATGGGACAA CCCAGAC                                          27

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GCCAGCAGAC TGGGAAACCA AGAC                                             24

(2) INFORMATION FOR SEQ ID NO: 15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GCCAGCAGTC TCCGACTGGG GGCTAACCAA GAC                                   33

(2) INFORMATION FOR SEQ ID NO: 16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Ala Ser Ser Leu Gly Ala Asn Gln Asp
1               5

PEPTIDES AND PHARMACEUTICAL COMPOSITIONS COMPRISING THEM

FIELD OF THE INVENTION

The present invention relates generally to peptide sequences, and methods of their use, which sequences modulate the activity of anti-idiotypic T cells. The activity of the anti-idiotypic T cells of interest is related to the ability of these T cells to recognize anti-p277 T cells. The peptides of the present invention thus comprise important tools in the effort to diagnose, prevent, alleviate or treat disease related to insulin-dependent diabetes mellitus (IDDM).

BACKGROUND OF THE INVENTION

Type I diabetes, or IDDM, is an autoimmune disease caused by T cells that attack and destroy the insulin-producing cells located in the islets of the pancreas (23). The autoimmune process culminating in IDDM begins and progresses without symptoms. The disease surfaces clinically only when the cumulative loss of β-cells exceeds the capacity of the residual β-cells to supply insulin. Indeed, the collapse of glucose homeostasis and clinical IDDM is thought to occur only after 80–90% of the β-cells have been inactivated by the immune system. Thus, patients who can be identified as suffering from IDDM are bound to be in an advanced stage of autoimmune destruction of their β-cells. Moreover, diagnosis of incipient, pre-clinical diabetes by the detection of immunological markers of β-cell autoimmunity can be made only after the onset of the autoimmune process. Therefore, the therapeutic quest is to find a safe, specific and effective way to turn off an autoimmune process that is already well underway.

The present inventors have examined this question before by studying the spontaneous diabetes developing in mice of the NOD strain, which is considered to be a faithful model of human IDDM (23–25). NOD mice develop insulitis around one month of age, which begins as a mild peri-islet infiltrate and progresses to severe intra-islet inflammation. Hyperglycemia, which attests to insulin insufficiency, begins in the females in our colony at about three months of age. By six months of age, almost all the female NOD mice have developed severe diabetes and most die in the absence of insulin treatment. Male NOD mice have a lower incidence of disease, for reasons that are not clear. The diabetes of NOD mice has been shown to be caused by autoimmune T cells (26).

T cell reactivity and auto-antibodies to various antigens have been detected in human IDDM patients as well as in NOD mice (27), and it is not clear whether immunity to any single one of the possible target antigens is the primary cause of the disease. Beyond the question of causation is the question of therapy.

It has been demonstrated that the initiation of the autoimmune process in NOD mice can be prevented by subjecting the mice, before the onset of diabetes, to various manipulations such as restricted diet, viral infections, or non-specific stimulation of the immune system (24). NOD diabetes is also preventable by induction of immunological tolerance in pre-diabetic mice to the antigen glutamic acid decarboxylase (GAD) (28, 29).

Anti-idiotypic T cells are T cells that recognize peptides derived from the antigen receptors of other T cells (6). It is thought that anti-idiotypic T cells are involved in regulating the activities of the T cells whose T cell receptor (TCR) peptides they recognize. Autoimmune T cells might be subject to regulation by anti-idiotypic T cells: anti-idiotypic T cells have been detected following intentional T cell vaccination of rodents in the model of experimental autoimmune encephalomyelitis (EAE) (6) or of humans (7) suffering from multiple sclerosis (MS) with autoimmune T cells.

European patent application 261,648 discloses the use of activated T cells specific for an autoimmune disease for the treatment of such disease. The T cells are preferably first pressure treated, subjected to a chemical cross-linking agent and/or subjected to a cytoskeletal disrupting agent in order to improve their immunogenicity. The entire treated cell or fraction thereof may be used as a vaccine against the autoimmune disease for which the T cell is specific.

In the known procedure for causing the arrest of autoimmune T cells, the subject is immunized with a sample of attenuated or avirulent T cells of the particular autoimmune specificity, or fragments or fractions thereof. The subject responds by activating regulatory T cells of at least two types: anti-ergotypic T cells that recognize T cell activation markers and anti-idiotypic T cells that appear to recognize the self-antigen receptors present on the pathogenic endogenous autoimmune T cells. T cell vaccination in experimental animals is effective in inducing permanent remission of established disease as well as in preventing disease. Use of peptide sequences of a T cell receptor β chain has been disclosed for vaccination of rats against experimental autoimmune encephalomyelitis (30, 31), thereby supporting the conclusion that the autoimmtme T cell receptor itself can supply a target epitope for regulator T cells.

In the present invention, it is shown that the spontaneous development of diabetes in NOD mice is regulated by an anti-regulated network in which the anti-idiotypic T cells are specific for a TCR VDJ peptide of an autoimmune T cell commonly expressed in mice of the non-obese diabetic (NOD) strain (1).

Functional Role of hsp60 and p277 Peptide in IDDM

The laboratory of the present inventors has previously demonstrated that an epitope of the 60 KDa heat shock protein (hsp60) is a target of autoimmune attack in the type I diabetes mellitus that develops spontaneously in the NOD strain of mice (2). This protein was formerly designated hsp65, but is now designated hsp60 in view of more accurate molecular weight information; by either designation, the proteins are the same. This laboratory has previously identified a peptide fragment from the human hspGo sequence, designated peptide p277 (SEQ ID NO:5), that contains a target epitope for T cells mediating diabetes (3; PCT publication WO 90/10449).

This laboratory has also isolated a clone of T cells, designated clone C9, that recognizes peptide p277 and can produce diabetes (3). Both the p277 peptide and the C9 T cells were found to have a functional role in controlling diabetes: vaccination of NOD mice with either attenuated C9 T cells or with peptide p277 could prevent (3) or even reverse diabetes (4). Both of these therapeutic vaccinations activate the anti-idiotypic regulator T cells.

SUMMARY OF THE INVENTION

The clone C9 was found to express a T cell receptor (TCR) β chain bearing an idiotope defined by its VDJ peptide sequence. Identical or similar VDJ sequences were shown to be shared by other diabetogenic T cells present in NOD and other strains of mice.

According to the present invention a peptide is disclosed having at least 7 and preferably about 7–24 amino acid residues comprising a "VDJ" region of the formula

V-D-J in which "V" includes the dipeptide sequence A-S, "D" includes the dipeptide sequence L-G, and "J" includes the tripeptide sequence N-Q-D, the italicized symbols representing the standard one-letter abbreviation for the corresponding amino acid. The D region preferably has 2–5 amino acid residues.

In specific embodiments of the present invention, the peptide comprises a segment "V", which includes the tripeptide sequence A-S-S. In others, the peptide comprises a segment "D", which includes the tripeptide sequence L-G-G, the tripeptide sequence R-L-G or the pentapeptide sequence L-G-L-G-A (residues 4–8 of SEQ ID NO:4).

In still another embodiment of the present invention, a peptide is provided having at least 7 and preferably 8–24 amino acid residues of the formula, Vβ-D-Jβ gene, in which the segment "Vβ" comprises from 1 to about 10 amino acid residues of the C-terminal end of a protein encoded by a Vβ gene, preferably a human Vβ gene, in which the last three C-terminal amino acid residues include the dipeptide sequence A-S; the "D" region has a total of 2–5 amino acid residues including the dipeptide sequence L-G, and the segment "Jβ" comprises from 1 to about 10 amino acid residues of the N-terminal end of a protein encoded by a Jβ gene, preferably a human Jβ gene.

Specific peptides include, but are not limited to, those, preferably having up to about 24 amino acid residues, which comprise the sequence A-S-S-L-G-G-N-Q-D (residues 47–55 of SEQ ID NO:1), A-S-R-L-G-N-Q-D (SEQ ID NO:3), A-S-S-L-G-L-G-A-N-Q-D (SEQ ID NO:4) and A-S-S-L-G-A-N-Q-D (SEQ ID NO:16).

Also contemplated by the present invention are certain DNA constructs that encode the peptides, including oligonucleotides that comprise a polynucleotide sequence complementary that least a portion of the above-mentioned DNA sequences. Likewise, pharmaceutical compositions comprising the peptides are contemplated, including preparations useful as vaccines or as agents for detecting the presence of anti-idiotypic T cells involved in the recognition of anti-p277 T cells.

The present invention is also directed to conjugates comprising the peptides and a second molecule, including a second peptide, polypeptide or small organic molecule.

As mentioned earlier, an important object of the invention is the disclosure of a method of modulating anti-idiotypic T cell activity in an individual. For example, the anti-idiotypic T cell activity is potentiated by the administration to the individual of an amount of a peptide of the invention effective to increase the activity of the anti-idiotypic cells.

The peptides of the present invention can also be used to activate T cells in vitro, preferably autologous T cells, which can then be re-administered to the patient to attack the T cells which are causing the disease.

Other objects of the present invention will be apparent to one of ordinary skill in view of the detailed description provided below, including preferred embodiments of the invention.

FIGSA. 5A and B Immunization to the C9 clone or to C9VDJ-flagellin boosts anti-idiotypic responses.

Figure 4A:
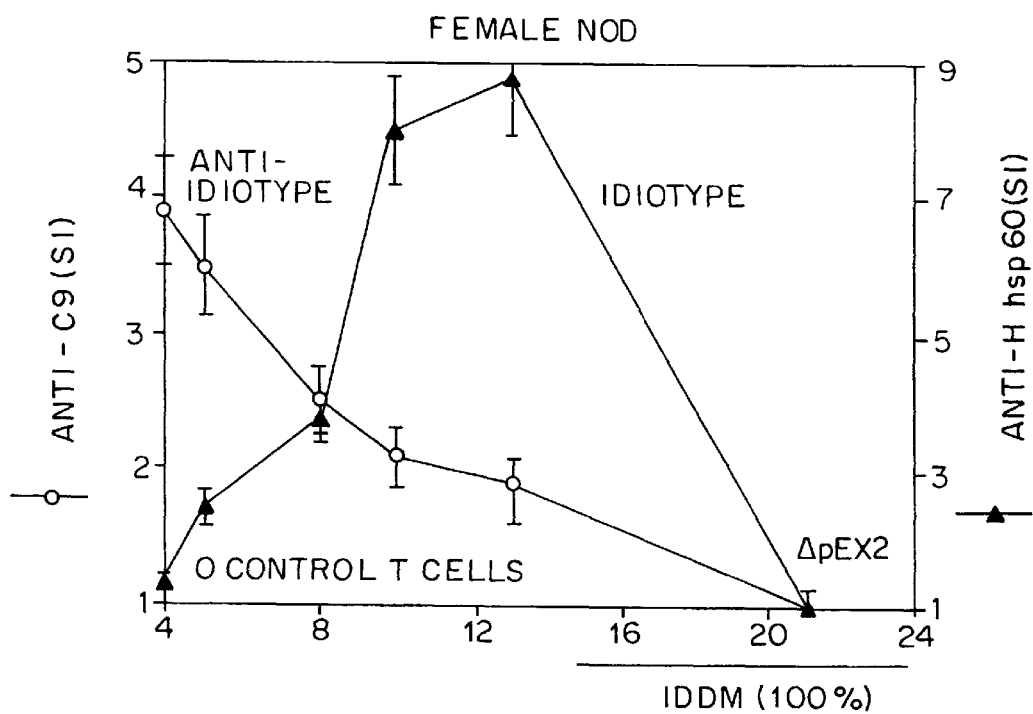
FIGS. 4A and B Spontaneous anti-idiotypic responses in naive female (FIG. 4A) and male (FIG. 4B) NOD mice. T cell responses to hsp60 (idiotype) and to the C9 clone (anti-idiotype) were measured in naive female and male NOD mice. Ten female and 10 male NOD mice were sacrificed at 4, 6, 8, 10, 13 and 21 week of age and their spleens were taken for a T cell proliferative assay. Spleen cells were tested at 200,000 cells/0.2 cc in microtiter wells for proliferative responses to either human hsp60 (5 μg/ml) or the C9 clone (20,000 cells/well irradiated at 5000 rad). The a proliferative response was measured by adding 3H-thymidine to the culture for the last 16 h of a 72 h stimulation. The incorporated 3H-thymidine was measured on a β-counter and the stimulation index (SI) was calculated as cpm incorporation in the presence of antigen/cpm incorporation in the absence of antigen. Individual mice were tested separately and the mean±SD for each time point was calculated.
Figure 4B:
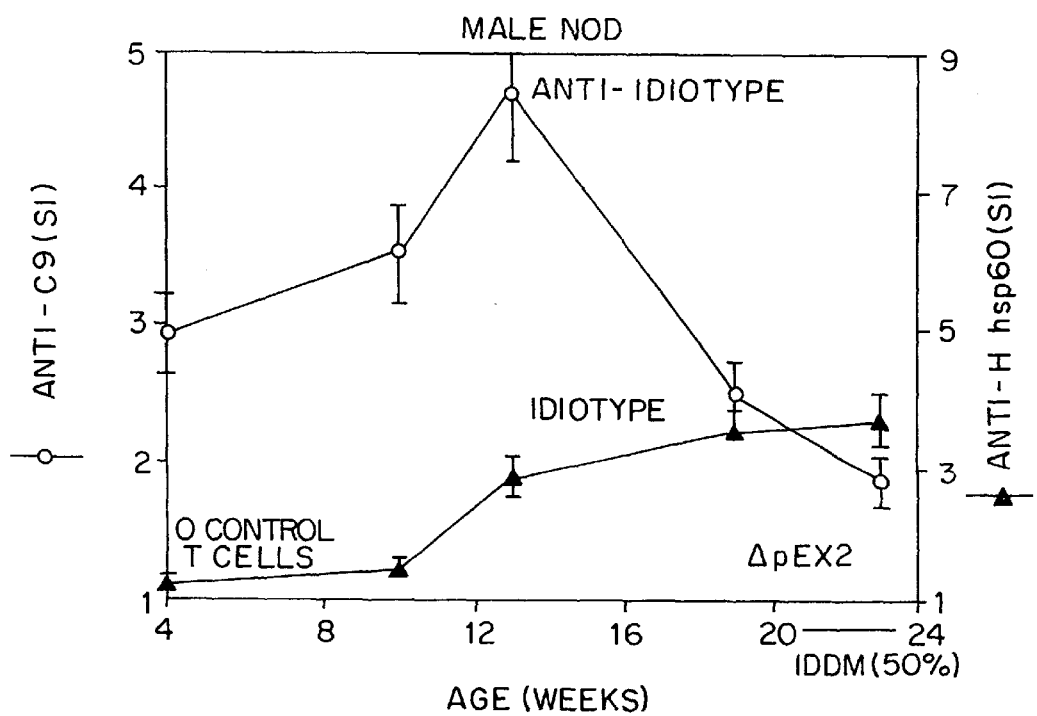
Figure 5A:
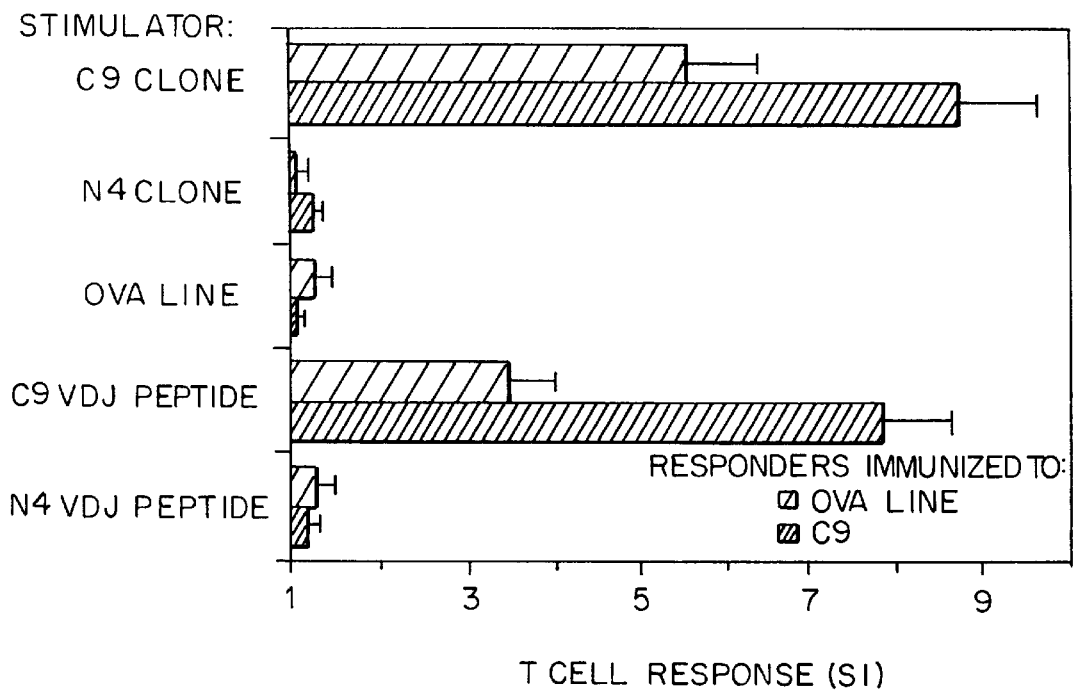

FIG. 5A NOD female mice, 9 weeks old, were immunized with either C9 clone cells or with an anti-OVA T cell line 5×10⁶ activated T cells in 0.1 ml PBS, intraperitonealy. Nine days later the spleens were removed for a proliferation assay, as described for FIG. 4. The antigens used in the proliferation assay were the C9 clone, the N4 clone, the anti-OVA line, all T cells at 20,000 cells/well irradiated with 5000 rad, the C9VDJ ASSLGGNQDTQY (residues 47–58 of SEQ ID NO:1) and N4VDJ ASSLWTNQDTQY (SEQ ID NO:2) synthetic peptides at 5 μg/ml.

Figure 5B:
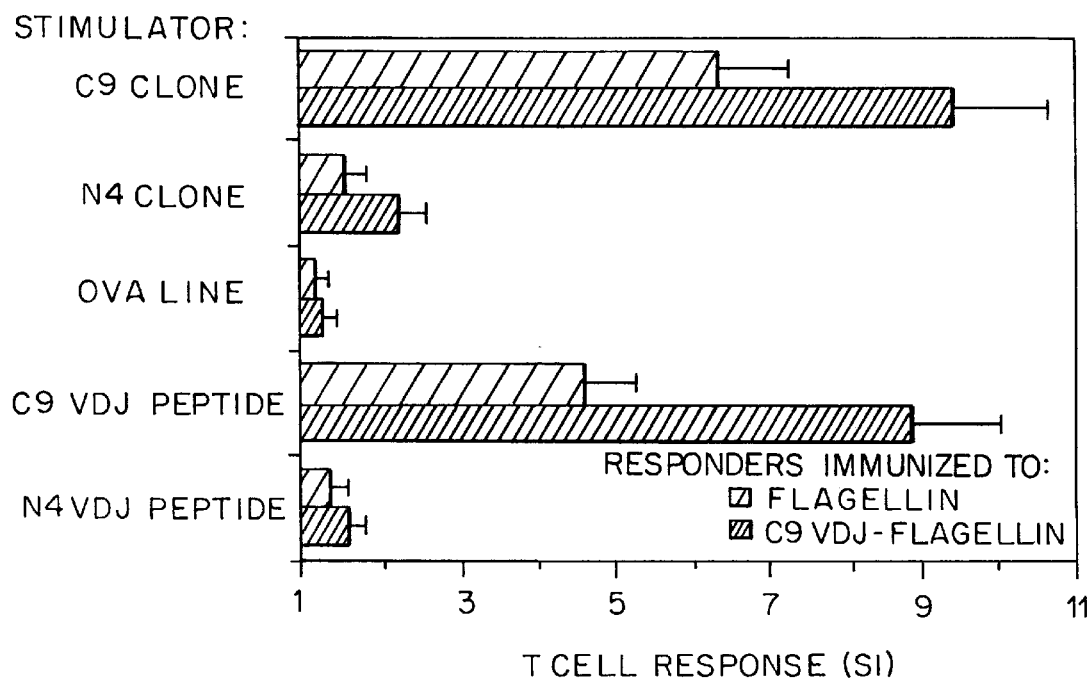

FIG. 5B NOD female mice, 9 weeks old, were immunized with either 100 μg of C9VDJ-flagellin or with flagellin only in 0.1 ml PBS, intraperitoneally. The proliferation assay was carried out as in FIG. 5A.

FIG. 6 Immunization with C9VDJ conjugated either to flagellin or to OVA induces anti-idiotypic responses. BALB/c or NOD 9 week old femal mice were immunized to flagellin, C9VDJ-flagellin or C9VDJ-OVA, 5 mice per group and 100 μg antigen per mouse, intraperitoneally. The C9VDJ-flagellin and flagellin were injected in 0.1 ml PBS and the C9VDJ-OVA was injected in an emulsion with 0.1 ml of IFA. Nine days later the spleens were removed and tested in a proliferation assay as described in the legend to FIG. 4. Proliferation responses were tested against the C9VDJ ASSLGGNQDTQY (residues 47–58 of SEQ ID NO:1) and N4VDJ ASSLWTNQDTQY (SEQ ID NO:2) synthetic peptides at 5 μg/ml.

Figure 7A:
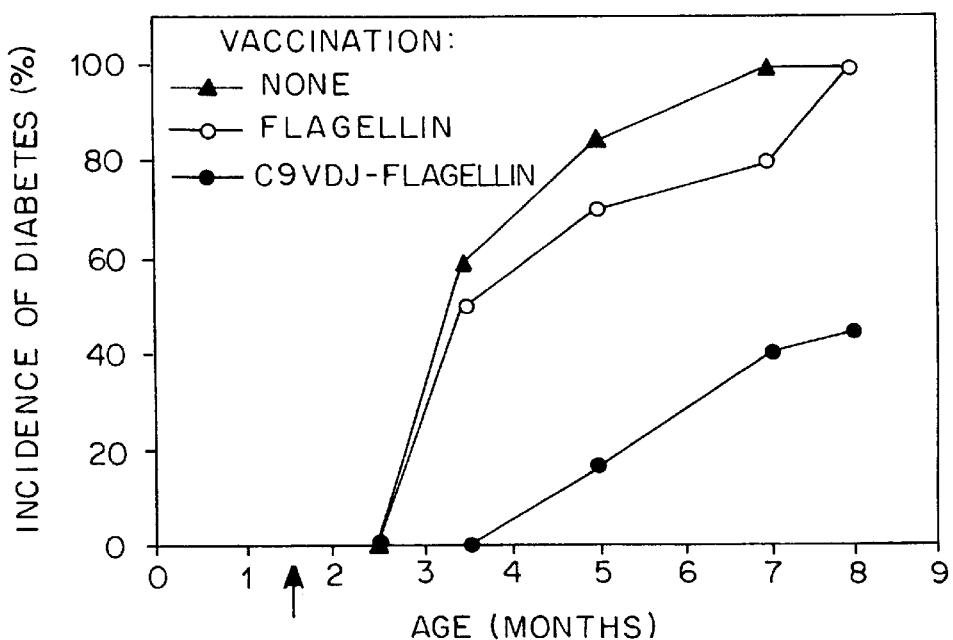

FIGS. 7A and B. Protection from diabetes by anti-idiotypic T cells.

FIG. 7A: Six week old NOD female mice were vaccinated with 100 μg of C9VDJ-flagellin alone in PBS, intraperitoneally, or left untreated, 10 mice per group. Diabetes was monitored by hyperglycemia from the age of 2 ½ months and onward, blood glucose levels exceeding 11.1 mmol/L were considered hyperglycemia.

Figure 7B:
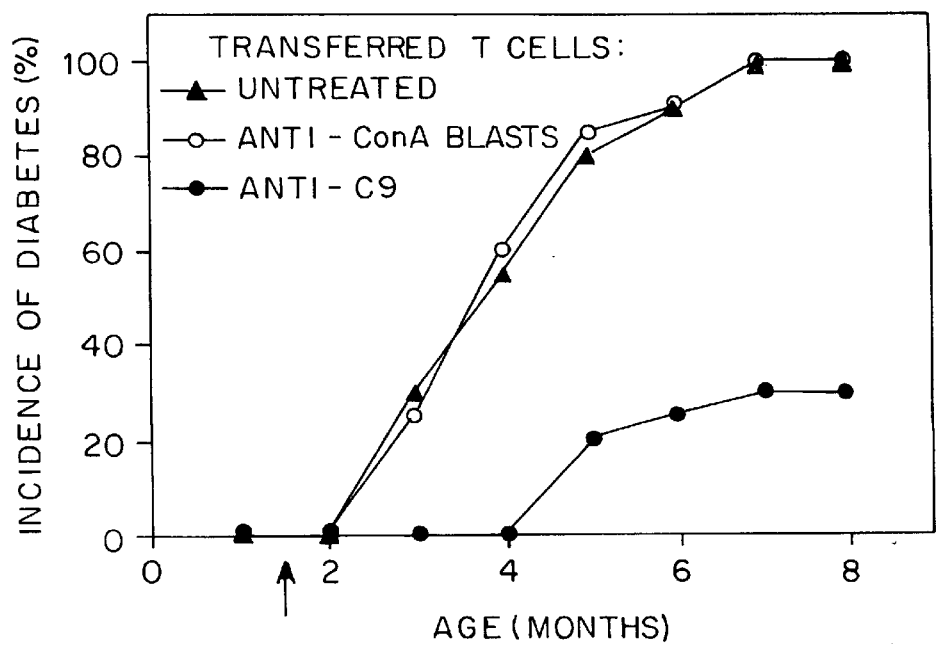

FIG. 7B: Ten NOD female mice, 5 week old, were inoculated with irradiated (5000 rad) C9 clone cells, $5\times10^6$ activated T cells in 0.1 ml PBS, intraperitonealy. Two weeks later the spleens were removed and the splenocytes pooled. Ten untreated naive NOD female mice of the same age were also sacrificed and their splenocytes were also pooled. The splenocytes from C9-inoculated mice were stimulated against the irradiated C9 clone, $8\times10^6$ splenocytes and $0.8\times10^6$ irradiated C9 clone cells per ml. The splenocytes from naive NOD mice were stimulated against irradiated ConA-selected T cell blasts of NOD females. After 48 h of stimulation the activated T cells were separated from inactivated cells by centrifugation on Lymphoprep (Nycomed, Norway), washed twice with PBS and injected, $10^7$ cells per mouse intraperitoneally, into 6 weeks old NOD female mice. Each group consisted of 10 mice, and 10 mice were left untreated. The development of diabetes was monitored as in FIG. 7A.

FIG. 8 Anti-C9 T cell line proliferation does not require APC. Anti-C9 T cell line was derived from splenocytes of naive 6 week old NOD females as described (3) by repeated stimulations with irradiated C9 T clone cells. An anti-OVA T cell line was derived from NOD female mice primed in vivo with OVA. The proliferation responses of these lines were tested at the 4th stimulation of the anti-C9 line and 17th stimulation of the anti-OVA line, 50,000 cells per well. The anti-C9 line was tested against activated and irradiated (5000 rad) C9 clone cell 50,000 per well and the anti-OVA line was tested against OVA (Sigma) 10 μg per well. APC were irradiated (3000 rad) NOD male splenocytes 200,000 per well. To ensure that the anti-C9 line or the C9 clone cells used in. the proliferation are not contaminated by APC, we used these cells as APC for the anti-OVA line. The proliferation assay was carried out as described for splenocytes in FIG. 4.

FIG. 9 Treatment with p277 peptide induces anti-C9 response. NOD female mice, 12 weeks old, were immunized with p277 or p278 in IFA, 100 g per mouse subcutaneously, or left untreated 10 mice per group. At 2 or 5 weeks after treatment 5 mice of each group were sacrificed their spleens removed and tested individually in a proliferation assay to C9VDJ peptide 5 μg/ml, as described in FIG. 4.

BRIEF DESCRIPTION OF THE TABLES

Table 1. Amino acid sequences of selected NOD and C57BL/6 lines. The different Vβ and Jβ segments are indicated. The amino acid and nucleotide sequence differences from the C9 VDJ rearrangement are marked by bold letters. The sequence of NOD clone 4-1-E.2 is taken from Nakano et al. (15).

Table 2. Tissue distribution of C9 VDJ and VJ in NOD mice of various ages detected by PCR amplification with specific oligonucleotide primers. nd=not done Table 3. Anti-idiotypic anti-C9 responses are both MHC class I and class II restricted. Five NOD female 6 weeks old mice were inoculated with $5\times10^6$ C9 clone cells, intraperitoneally. Nine days later the spleens were removed and the splenocytes pooled. The proliferative response of the splenocytes to either irradiated (5000 rad) C9 clone cells 20,000 per well or to the C9VDJ peptide 5 μg/ml. In order to determine the MHC restriction monoclonal antibodies specific to class I and II haplotypes were added, 2 mM of ammonium sulphate purified IgG. The following antibodies were used: anti-I-A: MKD6, anti-$K^c$: K9-18-10 and anti-$D^b$: 28-14-8. The % inhibition was determine as 100 (1-SI in the presence of antibody/SI without antibody).

DETAILED DESCRIPTION OF PREFERRED EMBODIMENTS

T cells involved in autoitnune diseases have been characterized by the genetic elements used to construct their autoimmune T cell receptors (TCR). In the present invention, the α and β chains of the TCR expressed by the C9 clone isolated from a naive, prediabetic NOD mouse were sequenced. Clone C9 specifically reacts to a defined peptide epitope (p277) of the 60 kDa heat shock protein (hsp60) molecule. The C9 clone is functional in NOD diabetes: activated C9 cells can adoptively transfer diabetes or, when attenuated, C9 can be used to vaccinate NOD mice against diabetes (3). It is shown here that the C9 TCRβ chain is comprised of the $V_\beta12$ variable (V) gene segment and the $J_\beta2.5$ joining (J) gene segment. The $V_\beta2$ sequence and the $V_\beta2.5$ sequence have been published and are known (32, 33). Thus, the sequence of the entire VDJ segment of the C9 TCRβ is as set forth in SEQ ID NO:1, including the L-G-G D segment.

The VDJ sequence of the C9 TCRβ chain is expressed in all our NOD mice. This VDJ sequence was detectable by two weeks of age in the thymus, and at one month of age in the spleen. The VDJ sequence was also found in the islet infiltrates in insulitis. Moreover, a C9-like VDJ sequence was isolated from among the anti-p277 T cells derived from C57BL/6 mice with diabetes induced by active immunization to the p277 peptide. Interestingly, the C9-like VDJ sequence could be expressed conjoined to different Vβ gene segments. The published sequence of a diabetogenic NOD T cell clone, of unknown specificity, isolated independently in Japan, shows a β chain that differs from that of C9 by only two amino acids (15). A diabetic human T cell clone also was found to bear a similar VDJ motif (21, 22). Thus, the C9 VDJβ joining region sequence appears to be a common element in autoimmune TCR associated with both the spontaneous diabetes of NOD mice and humans and the induced diabetes of C57BL/6 mice.

Mice of the NOD strain spontaneously develop autoimmune insulitis at about 1 month of age which progresses several months later to overt insulin-dependent diabetes mellitus (IDDM) (1). The present inventors have discovered and previously published that regulation of the autoimmune IDDM process can be influenced by two factors: by T-cell immunity to the p277 peptide of the 60 KDa heat shock protein (hsp60) (2) and by anti-idiotypic T cells that recognize the anti-p277 T cells (3). Overt IDDM in NOD mice is preceded by spontaneous T cell activity to peptide p277 corresponding to position 437-460 of the human hsp60 sequence; T cell clones reactive to p277, such as clone C9, can adoptively transfer hyperglycemia and early insulitis, and vaccination with the p277 peptide itself can prevent (3) or even reverse IDDM (4). Treatment with peptide p277 was marked by down-regulation of the anti-p277 immunity. Thus, T cell immunity to p277 appears to be functionally involved in NOD diabetes.

The function of p277 immnity in mouse diabetes was extended by experiments showing that male mice of the non-diabetic C57BL/6 strain could be induced to develop insulitis and hyperglycemia by immunization to p277 conjugated to carrier proteins such as OVA or BSA (5). Anti-p277 T cell lines were found to adoptively transfer diabetes to naive C57BL/6 mice.

With regard to regulation of NOD diabetes by anti-idiotypic T cells responsive to C9 anti-p277 T cells, we have found that the C9 clone, when attenuated, can be used to vaccinate NOD mice against IDDM (3). Since the regulatory effects of T cell vaccination have been related to the TCR of the vaccinating T cells (6,7), the present investigation was directed to the TCR of the prototype anti-p277 C9 T cell clone to determine the sequence of its α and β chains and to investigate the distribution of the C9 TCR among various T cell populations of NOD mice. The characteristic VDJ sequence of the C9 TCR β chain was also studied in the T cells of C57BL/6 mice responsive to p277, and was compared to other published TCR sequences.

These investigations have led to the determination of the sequence of the VDJ gene segment of the C9 TCR β chain, i.e., SEQ ID NO:1. It has been determined that the nonapeptide, including the C-terminal three amino acids of the V segment, the three residues of the D segment and the N-terminal three amino acids of the J segment (residues 47–55 of SEQ ID NO:1), comprise the immunogenic portion of the C9 TCRβ chain. This peptide has been shown to cause a substantial down-regulation of diabetes in the NOD mouse model. It can also be used for the early diagnosis of IDDM and for the monitoring of p277 treatment of IDDM.

The VDJ region of several other clones was also studied which clones also recognized the p277 peptide of human hsp60, were diabetogenic, and could vaccinate NOD mice against developing diabetes. These were found to have the same VDJ sequence as was established for C9. Another cell line, the N4 line, which is neither diabetogenic nor vaccinates against diabetes, has a sequence which differs from that of the CD9 peptide in that 2 of the 3 peptides of the D region differ Leu-Trp-Thr as opposed to Leu-Gly-Gly).

The VDJ sequence of another NOD clone, 4-1-E.2, has recently been published (15), which clone was reported to transfer insulitis into diabetes free 1-E+ transgenic NOD mice. Thus, it is assumed that the VDJ region of the TCRβ chain of this clone will also be operable to activate T cells which recognize the autoimmune T cell. The reported sequence for this TCRβ chain lacks one serine in the C-terminus of the V segment, has the same tripeptide at the N-terminus of the J segment, and has the tripeptide Arg-Leu-Gly as the D segment. Thus, this sequence shares the Leu-Gly dipeptide in the D segment of the C9 TCRβ, and shares the Ala-Ser dipeptide of the C terminus of the V segment with the C9 TCRβ chain.

The VDJ region of anti-p277 T cell lines derived from splenocytes of diabetic C57BL/6 mice were also studied in view of the fact that these cell lines could adoptively transfer insulitis and hyperglycemia. As can be seen from Table 3, the C-terminus of the V segment and the N-terminus of the J segment are the same as for C9, while the D segment is Leu-Gly-Leu-Gly-Ala (residues 4–8 of SEQ ID NO:4). As this clone recognizes the autoimmune T cells it is expected that the peptide of SEQ ID NO:4 can be used in the same manner as the peptide of residues 47–55 of SEQ ID NO:1. Furthermore, as the Leu-Gly dipeptide repeats, it is assumed that a synthesized Leu-Gly-Ala D segment will operate in the same manner as the C9 sequence in which the D segment is Leu-Gly-Gly. Thus, the nonapeptide of SEQ ID NO:16 is also operable in accordance with the present invention.

In light of what has been determined as to the sequence of the VDJ region of clones which are known to be diabetogenic as compared with those which are not, the preferred embodiment of the present invention is a peptide having a minimum of seven amino acid residues of the formula V-D-J in which "V" includes the dipeptide A-S, "D" includes the dipeptide sequence L-G and "J" includes the tripeptide sequence N-Q-D. The D region preferably has 2–5 amino acids. Preferably the V segment tripeptide including the A-S dipeptide, is immediately adjacent to the D segment and the N-Q-D tripeptide of J is immediately adjacent the D segment.

The peptide of the present invention may have as many as about 24 amino acids. Preferably, any additional amino acids of the V segment correspond to the sequence of the $V_\beta 12$ gene segment (32) and any additional peptides in the J segment correspond to the $J_\beta 2.5$ segment (33).

Besides the preferred peptide residues discussed above, sequences which substantially correspond thereto in which one or more amino acids are deleted, added or replaced with other amino acids are intended to be encompassed by the present invention as long as they have the ability to immunologically cross-react with the original peptide such that T cells activated thereby recognize and down-regulate autoimmune anti-p277 T cells.

In order to substantially correspond to such peptide, the changes in the sequence of any of the preferred peptides of the present invention must be relatively minor. Thus, peptides substantially corresponding to the disclosed peptides of the present invention can readily be synthesized and screened for the appropriate bio-activity. The most appropriate experiment to be used to screen for the biological activity of being able to serve as a vaccine to down-regulate diabetes is to actually test the construct by vaccination of NOD mice and determining whether such vaccination is effective in inhibiting the disease in the manner described herein with respect to the experiment the results of which are shown in a FIG. 7 In view of the fact that the critical region is relatively short, it would not take undue experimentation to make minor substitutions, additions and deletions and screen the product for the appropriate biological activity, particularly in light of the motif information which can be gleaned from Table 3.

Besides the peptides discussed herein, salts and functional derivatives thereof having the ability to immunologically cross-react with said peptides may also be used.

As used herein the term "salts" refers to both salts of carboxyl groups and to acid addition salts of amino groups of the protein molecule. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the protein, do not confer toxic properties on compositions containing it and do not adversely affect the antigenic properties thereof.

These derivatives may, for example, include aliphatic esters of the carboxyl groups, amides of the carboxyl groups by reaction with ammonia or with primary or secondary amines, N-acyl derivatives of free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The therapeutic use of the peptides in accordance with the present invention is as a vaccine for the treatment of IDDM and incipient IDDM. When administered with an appropriate immunogenic adjuvant, such as oil, so as to induce an immunogenic response, T cells are raised which can down-regulate the autoimmune anti-p277 T cells. If the patient is shown to already be in the pre-clinical incipient stages of IDDM, injection with a peptide in accordance with the present invention can create a down-regulation of autoimmunity and thus arrest the autoimmune process before significant peraanent damage is done. Vaccination with the peptide in accordance with the present invention can also be used as a therapeutic agent to arrest the autoimmune process even after it is far advanced, as shown recently by the laboratory of the present inventors regarding the treatment of NOD mice with the peptide p277 (4).

The present invention also provides a pharmaceutical composition for the prevention or treatment of IDDM comprising a pharmaceutically acceptable carrier and, as active principal, an effect amount of a peptide in accordance with the present invention, a salt or a functional derivative thereof. The pharmaceutically acceptable carrier is preferably an oil vehicle such as an emulsion of mineral oil known as incomplete Freund's adjuvant (IFA). However, IFA, as well as complete Freund's adjuvant (CFA; a preparation of mineral oil containing various amounts of killed organisms of Mycobacterium) are not desirable for human use because the mineral oil is not metabolizable and cannot be degraded by the body. It has recently been found that certain fat emulsions, which have been in use for many years for intravenous nutrition of human patients, can also act as a vehicle for peptide therapy using the peptides of the present invention. Two examples of such emulsions are the available commercial fat emulsions known as Intralipid and Lipofundin. "Intralipid" is a registered trademark of Kabi Pharmacia, Sweden, for a fat emulsion for intravenous nutrition, described in U.S. Pat. No. 3,169,094. "Lipofundin" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin.

Besides using the peptides of the present invention as a vaccine by direct administration, the peptides of the present invention can also be used to activate the autologous T cells of a patient with IDDM or incipient IDDM. Thus, autologous T cells are obtained from the IDDM patient to be treated, preferably by separation from the peripheral blood. Such T cells are then activated by in vitro contact with a peptide in accordance with the present invention by means which are known to those of ordinary skill in the art. Such specific and activated T cells are then administered to the same patient from whom they were originally obtained in order to down-regulate the autoimmune T cells.

The present invention also comprehends a composition of such specific and activated T cells. The administration of such T cells effectuates passive immunization against the autoimmune T cells, thereby down-regulating the autoimmune process. It is not necessary to obtain a complete cure of IDDM for the present invention to be useful. As long as some down-regulation of the autoimmune process is obtained, the therapeutic compositions and methods of the present invention have a practical utility.

The peptides of the present invention are also useful for the early diagnosis of diabetes, preferably in the pre-clinical stage or shortly after clinical diagnosis, as well as for staging the disease and for monitoring the course of the immunological treatment of IDDM and particularly p277 treatment. If the serum of the patient in question includes T cells which proliferate or otherwise exhibit their immunological function, such as by expressing cytokines upon contact with the peptide of the present invention, this is a sign of the existence of the disease. As seen in FIG. 4, the anti-idiotype antibodies are present in the greatest quantities in the early stages of the disease. Furthermore, a quantitative or semi-quantitative analysis of the number of such T cells in a patient correlates with the efficacy of the down-regulation treatment. The greater the quantity of such T cells, the better the course of treatment. Thus, if the number of such antibodies increase over time, the treatment is being effective. If the number decreases, the treatment is not as effective and should be modified to try to cause an increase in the quantity of such T cells.

Accordingly, the present invention further comprehends methods of diagnosis and staging of IDDM and monitoring the course of treatment thereof.

EXAMPLE

Materials and Methods

Animals

NOD/L: mice were raised in our animal facilities at the Weizmann Institute of Science. The breeding nucleus was the gift of Dr B. H. Leiter. C57BL/6 and BALB/c mice were obtained from Jackson Laboratories, Bar Harbor, Me, USA.

Antigens

OVA was purchased from Sigma Chemical Co., St. Louis, Mo, USA. Recombinant human hsp60 was kindly provided by Dr. Ruurd van der Zee of the University of Utrecht. The synthetic peptide p277 VLGGGCALLRCIPALDSLT-PANED (SEQ ID NO:5) was synthesized by standard Fmoc chemistry, purified on HPLC by reverse phase chromatography using a CM12 column (Merck, FRO). The sequence was confirmed by amino acid analysis. Peptide p277 was conjugated to OVA by 1-ethyl-3-(3-dimethylaminopropyl) carbodiimide (EDC, Sigma Chemical Co., St. Louis, Mo., USA) as described (8).

Immunization

C57BL/6 male mice 6–8 weeks old, were injected s.c. with 50 $\mu$g of p277-OVA conjugate emulsified in IFA (Difco, Detroit, Mich., USA) in a total volume of 0.2 ml. Mice were bled 2, 3, and 4 weeks after the immunization and blood glucose was tested using a Beckman Glucose Analyzer II (Beckman, Palo Alto Calif., USA). Hyperglycemia was defined as a plasma glucose concentration greater than 11.1 mmol/L measured at 10 h under non-fasting conditions. This concentration of glucose was chosen as boundary of hyperglycemia because it was greater than 3 SD above the mean plasma glucose concentration measured in 200 untreated non-diabetic mice (5).

T cell lines

The NOD T cell lines and clones, obtained from pre-diabetic NOD spleens, were selected in vitro by their response to recombinant hsp60, as described (3). A NOD anti-OVA T cell clone awas generously provided by Dr. Anne Cooke, Cambridge England. Anti-p277 and anti-OVA T cell lines were prepared from the draining lymph nodes of C57BL/6 mice on day 9 after immunization as described previously (3). We have shown that hyperglycemia can be adoptively transferred by C9 and other anti-p277 T cell clones of NOD mice (3) and by anti-p277 T cell lines of C57BL/6 mice (5).

RNA and cDNA Preparations

Cell lines

Following a 3-day activation by incubation with p277 as described (3), T cell blasts were collected and separated from cell debris and accessory cells on a ficoll gradient, washed in PBS and cultured for 2 more days in medium containing 10% T cell growth factor as described (3) to ensure that the cultures contained only living T cells. The T cells were then collected, washed in PBS and snap frozen in liquid nitrogen. Each sample was homogenized and total RNA extracted by the RNAzol kit (Cinna/Biotecx, Friendswood Tex., USA). Approximately 5 µg of total RNA was transcribed into first strand cDNA in a 20 µl reaction of the cDNA cycle kit (Invitrogen, San Diego Calif., USA) using oligo dT as a primer.

Spleen and Thymus

Spleens and thymuses were removed from NOD/L: female and male mice and C57BL/6 male mice, and immediately frozen in liquid nitrogen. Preparation of RNA and cDNA was performed as above.

Pancreatic Islets

Pancreatic islets were prepared from female NOD mice by the method of Gotoh (9). Briefly, collagenase was injected into the bile duct, the duct was then ligated and the pancreas excised. Collagenase digestion was carried out in a shaking water bath at 37° C. for 30–45 minutes and the tissue was then washed extensively in PBS. The islets were hand-picked from the digest using a dissecting microscope and frozen in liquid nitrogen. RNA and cDNA preparation was carried out as above.

PCR Amplification

Vβ Panel

Three µl of the cDNA preparation were put into a reaction mixture containing PCR buffer, 1 µM dNTP mixture, 1 µM of Cβ primer (Operon Technologies, Alameda, Calif., USA) and 2 U/ml Taq polymerase (USB, Cleveland Ohio, USA). This mixture was distributed into 19 reactions tubes, each containing a different Vβ-specific oligonucleotide primer, obtained from Operon Technologies (Alameda, Calif., USA). The final concentration of the primer was 1 µM. The amplification was carried out in a DNA thermocycler (Perkin Elmer) for 30 cycles. The cycle profile was as follows: Denaturation at 94° C. for 60s, annealing at 55° C. for 60s and elongation at 72° C. for 60s. Eight ml of each amplification reaction were subjected to electrophoresis on a 2% agarose gel (FMC, Rockland Me., USA), stained with ethidium bromide (Sigma Chemical Co., St. Louis, Mo., USA), and visualized with UV light. In-gel hybridization (10) was performed for one hour with 0.5 pmol/ml of a $^{32}$P-labeled oligonucleotide probe specific for Cβ. The amplified products were sequenced directly according to Casanova et al. (11) with the Sequanase™ version II kit (USB).

C9 VDJβ Specific Oligonucleotide

The C9 VDJβ-specific and other oligonucleotides were synthesized in the Department of Molecular Biology and Genetic Engineering, Hadassah Hospital, Mount Scopus, Jerusalem, Israel. The sequence of the C9 VDJβ specific oligonucleotide was: 5'-TTAGGGGGTAACCAAGAC-3' (bases 10–27 of SEQ ID NO:6). One µl of each cDNA sample tested was put into the reaction mixture containing the C9 VDJβ oligonucleotide and the Cβ oligonucleotide as primers and analyzed as above. A higher specificity was achieved by raising the annealing temperature to 65° C. A $^{32}$P-labeled C9 VCJβ specific oligonucleotide was used as a probe in in-gel hybridizations with a Vβ panel amplified by PCR as described (10).

C9 Vα Amplification

Five µl of the C9 cDNA first strand preparation were tailed with dGTP using terminal transferase (TdT) under the conditions recommended by the manufacturer (Boehringer Mannheim, FRG) and 100 nM of dGTP in a total volume of 50 µl for 30 min. Ten µl of the tailing reaction were put in an anchored PCR reaction according to Acha-Orbea et al. (12). The sequence of the first PCR Cα oligonucleotide primer (Cα1) was: 5'-TGGCGTTGGTCTCTTTGAAG-3' (SEQ ID NO:7) and the sequence of the nested oligonucleotide primer (Cα2) used for the second PCR amplification was: 5'-CGGCACATTGATTTGGGAGTC-3' (SEQ ID NO:8). The amplification product was detected with the oligonucleotide probe (Cα3): 5'-ACACAGCAGGTTCTGGGTTC-3' (SEQ ID NO:9) cloned into pBluescript SK(+) (Stratagene), and sequenced according to the user manual of the Sequenase™ Version II kit.

C9 VJα Specific Nucleotide

A C9 VJα specific oligonucleotide with the sequence 5'-ATGAGAGGGCCTAATTAC-3' (SEQ ID NO:10) was synthesized and used as a primer together with the Cα2 primer for PCR amplification of different lines, as described for the C9 VDJβ amplification.

Results

The TCR Nucleotide Secuence of C9

To determine the nucleotide sequence of the α and α chains of the C9 TCR, cDNA was prepared from the mRNA extracted from the C9 clone. PCR amplification was performed using a Cβ constant region oligonucleotide primer and each of 20 Vα specific oligonucleotide primers.

Figure 1:
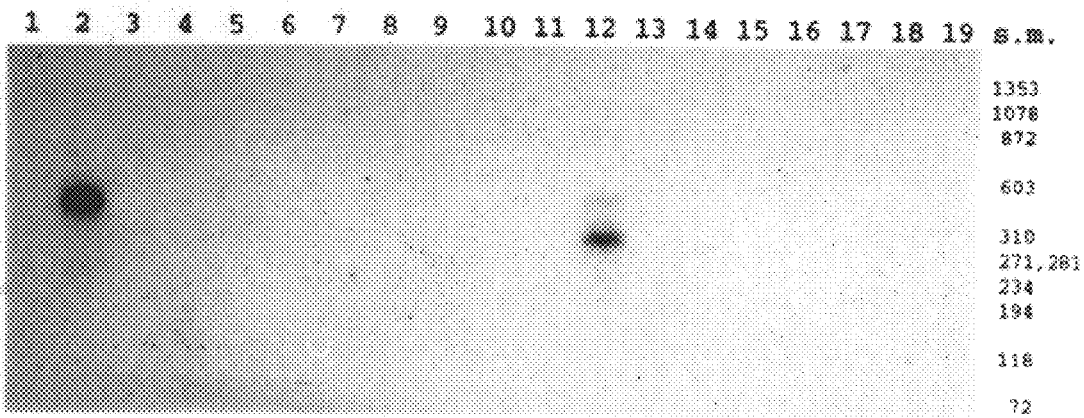
FIG. 1 Determination by PCR of TCR Vβ0 gene usage in the C9 clone. Lanes 1–19: the 19 different Vβ amplification reactions with the Cβ oligonucleotide primer. Lane s.m.: fx/Hae III size marker. The gel was hybridized with an internal Cβ oligonucleotide probe and therefore the size marker is printed. The two positive bands for Vβ2 and Vβ12 indicate the existence of these segments in the C9 clone.

Of the 19 different Vβ amplification reactions, only Vβ2 and Vα12 PCR amplification products were visible (FIG. 1). After direct sequencing of both PCR products, the Vα2 was found to be nonproductive (out of reading frame). In contrast, the Vβ12 was in frame and thus productive (Table 1).

The greater number and variability of the α chain V-region made a similar panel amplification approach unworkable. Therefore, to sequence the α chain, we used an anchored PCR with dGTP tailed cDNA employing nested constant region oligonucleotide primers. The VJα sequence of C9 was found to be MRGPNW (SEQ ID NO:11); the Vα was BNB (13) and the Jα was 16 (14).

TCR Usage in other NOD T Cell Lines

We studied other T cell lines derived from the same pool of NOD lymphocytes that generated the C9 clone. The C7, N1 and N26 lines that recognize the p277 peptide of human hsp60 were diabetogenic and could vaccinate NOD mice against developing diabetes (3). We also studied the N4 line that reacts to *M. tuberculosis* hsp65 but not to human hsp60, and is neither diabetogenic nor vaccinates against diabetes (3), and an unrelated anti-OVA line.

Figure 2:
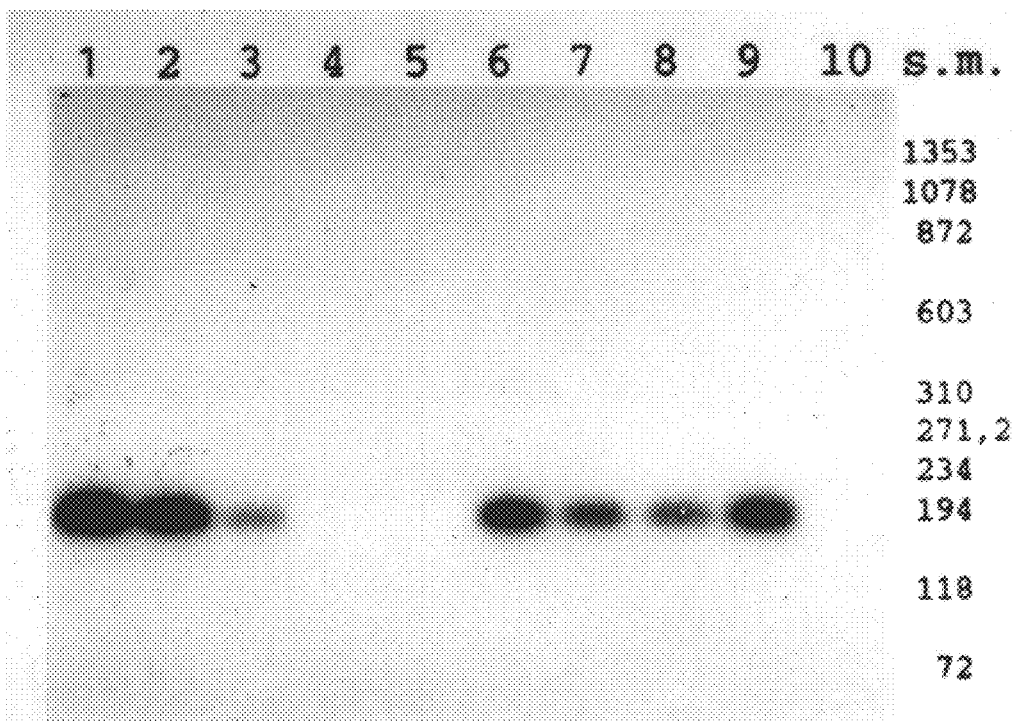
FIG. 2 The presence of sequences homologous to the C9 VDJ rearrangement determined by PCR in different T-cell lines using the specific C9 VDJ oligonucleotide primer. The first four lanes show the results of the NOD lines C9 (lane 1), C7 (2), N4 (3), and an anti-ovalbumin line (4). The next lanes show the C57BL/6 anti-p277 lines obtained after different numbers of stimulation cycles: 1 stimulation (lane 5), 2 stimulations (lane 6), 5 stimulations, two different lines (lane 7 and lane 8) and 6 stimulations (lane 9), and the C57BL/6 anti-OVA line (lane 10). Note that there is no signal from both the NOD and C57BL/6 anti-OVA lines (lanes 4 and 10) nor from the first anti-p277 stimulation of the C57BL/6 line (lane 5). The weak signal obtained from the related N4 clone (lane 3) demonstrates the accuracy of the assay.

Since the CDR3 regions of the α and the β TCR chains can each contribute to an idiotope, we prepared specific oligonucleotide probes based on the VJα and the VDJβ regions of the C9 clone. Using the α constant region and the VJα oligonucleotide primers, we obtained PCR amplification only for the anti-p277 T cell line. The β chain constant region and the VDJβ oligonucleotide primers resulted in PCR amplification for all the anti-p277 T cell lines. However, a faint amplification band could be detected for the N4 line (FIG. 2, lane 3). Anti-OVA lines generated from NOD or from C57BL/6 mice were negative (FIG. 2, lanes 4 and 10).

For further analysis, we used the panel of 19 Vβ specific and the β chain constant region oligonucleotide primers for PCR amplification. In all the NOD anti-p277 T cell lines we found, among others, a Vβ12 amplification that was sequenced and found identical to the C9 Vβ. Amplification of cDNA derived from the N4 cell line produced, among others, a Vβ11 PCR product. Sequencing of the product revealed a VDJβ region similar to the C9 VDJβ except for a difference in 3 bp as can be seen in Table 1. Note that the very similar VDJ sequences of C9 and N4 were the rearrangement products of 2 different Vβ genes. The minor difference in the VDJ sequence of C9 and N4 resulted in noticeably different PCR amplifications (FIG. 2), demonstrating the usefulness of the PCR primer as a means for screening for the C9 idiotope and related sequences.

Table 1 also includes the β chain VDJ sequence of an NOD clone, 4-1-E.2, published by Nakano and associates (15). This clone was reported to transfer insulitis into diabetes-free 1-E+ transgenic NOD mice. However, its specific antigen was not reported. Note that 4-1-E.2, like C9, expresses the Vβ12 Jβ2.5 genes and has a VDJ sequence similar to that of C9: C9-ASSLGGNQD (residues 47–55 of SEQ ID NO:1); 4-1-E.2-ASRLGNQD (SEQ ID NO:3).

Distribution of the C9 VDJβ and VJα Seauences in NOD Tissues

In our NOD colony, insulieis is first evident around the age of 1 month. The intensity of the insulitis progresses and the insulin-producing β cells are destroyed. The female mice begin to develop overt hyperglycemia at about 3 months of age and by 6 months of age essentially all the female mice are clinically ill and die unless treated with insulin. Male mice manifest a lag in the progression of insulitis and only about 50% develop overt IDDM. To see whether the presence of the C9 VDJβ rearrangement could be correlated with the progression of the autoimmne disease, we prepared cDNA from spleens and thymuses of 0.5, 1, 2, 3 and 4 month old NOD mice, pooling the organs of 5 mice in each age group. Islets were studied from 1 and 2 month old NOD females. The cDNA samples were amplified by PCR using the VDJβ or the VJα primers and the corresponding constant region primer. All the VJα-primed PCR reactions were negative; but VDJβ-primed PCR produced amplifications in both female and male NOD mice. The results are summarized in Table 2. The thymus preparations were positive at all ages in both males and females. In the spleens, the C9 rearrangement was evident from the age of 1 month in the females and from 2 months in the males. The VDJβ was also detected in inflamed islets. Thus, the C9 VDJβ probe seems to detect an idiotype shared by individual NOD mice. The progression of the C9 VDJβ specific signal from the thymus to the spleen and islets seems to correlate with the progression of the disease process.

TCR β usage in Anti-p277 T Cell Lines of C57BL/6

Since p277 plays a role in NOD mouse diabetes, we tested whether immunization against this peptide induces disease in mice that are not prone to diabetes and found that p277 conjugated to a protein carrier could induce hyperglycemia, insulitis and insulin autoantibodies in C57BL/6 mice (5). We therefore established anti-p277 T cell lines derived from splenocytes of diabetic C57BL/6 mice that had been immunized to p277/OVA. The lines were propagated in microtiter wells and repeatedly stimulated with p277 in the presence of irradiated autologous splenocytes. The resulting T cell lines could adoptively transfer insulitis and hyperglycemia, but the control anti-OVA T cell line could not (5).

We analyzed the Vβ usage of the anti-p277 lines after 1, 2, 5 and 6 stimulations with p277. Following each stimulation, samples of several wells were pooled for analysis and further culture. As described above, cDNA was prepared and used for Vβ panel amplification. The first two stimulations yielded productive amplification for practically all the Vβ primers. Two distinct samples following the fifth stimulation showed a more restricted Vβ usage: 1, 2, 6, 7, 9 and 19 for one and 1, 14, 15, 16 and 18 for the other. After the sixth stimulation a restricted amplification array was found: 3, 5, 7, 8 and 11. Thus, no particular Vβ was associated with p277 recognition.

Figure 3A:
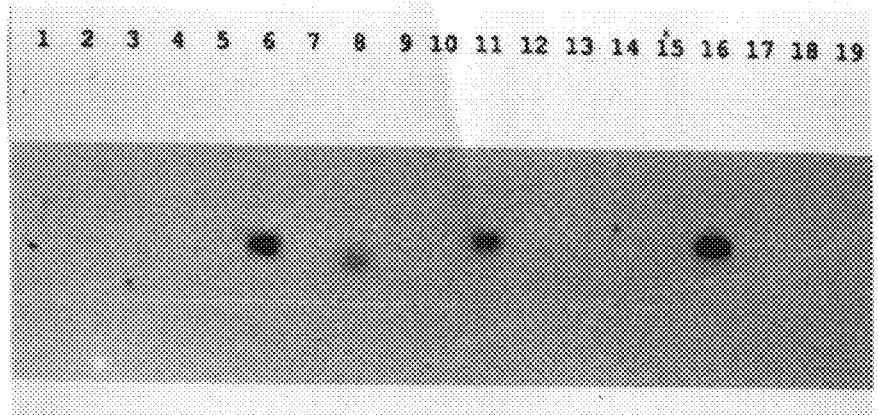
FIGS. 3A and B Presence of sequences homologous to the C9 VDJ rearrangement in the PCR amplifications of anti-p277 C57Bl/6 lines. A Vβ panel amplification, as described in FIG. 1, was performed with the cDNA samples of the anti-p277 C57BL/6 lines after 2 stimulations (FIG. 3A) and 6 stimulations (FIG. 3B). In-gel hybridization was made with the C9 VDJ specific oligonucleotide probe.
Figure 3B:
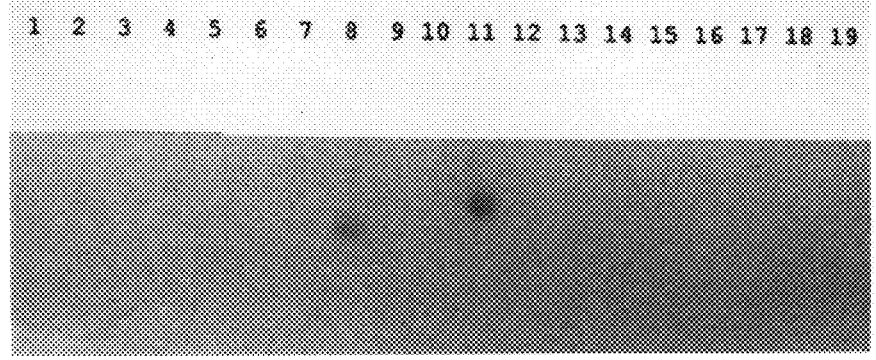

A PCR amplification with the C9 VDJβ and the Cβ region oligonucleotide primers was performed with the cDNA samples of the different stimulations. FIG. 2 shows positive amplification in all but the first stimulation (lane 5). To find which of the Vβ amplifications contained the C9-like VDJβ rearrangement, we hybridized the second and sixth stimulation PCR panels with the C9 VDJβ oligonucleotide probe. As can be seen in FIG. 3A, Vβ6, 8, 11 and 16 hybridized with the probe in the second stimulation, but in the sixth stimulation (FIG. 3B), only Vβ8 and 11 were positive. Vβ6 amplification product from the second stimulation was cloned and its VDJ sequence was found to have some similarity to the C9 VDJβ (Table 1). Six additional, but unrelated VDJβ sequences were also obtained (not shown). We also screened thymus and spleen cells of naive 2 month old male C57BL/6 and BALB/c mice using the C9 VDJβ oligonucleotide primer. The thymus and spleens of C57BL/6 were positive. However in the BALB/c mice, only the thymus was positive.

Validation of the VDJ PCR Probe

In this study, the sequence of the RNA coding for the α and β chains of the TCR of the diabetogefic NOD clone C9 were determined and VJα and VDJβ probes were used to detect TCR sequences related to those of C9 in various T cell populations. The specificity of the C9 VDJβ primer was indicated by hybridization of this oligonucleotide with the products of β chain PCR amplification using Vβ and Cβ primers. The reliability of the PCR primed with the C9 VDJβ oligonucleotide was confirmed by examining the TCR sequences of the targets involved: the N4 clone, which has a 3 bp difference (2 amino acids) from the C9 VDJβ primer, gave only a faint PCR product (FIG. 2) while the C57BL/6 anti-p277 line, which contained a clone that also had a 3 bp difference (Table 1), gave a more prominent PCR signal. However, the 3 nonhomologous nucleotides from the B6 clone reside closer to the 5' end of the C9 primer sequence than the 3 bp nonhomologous nucleotides of the N4 VDJβ resulting possibly in a more efficient amplification under stringent conditions. Thus, we may conclude that our C9 VDJβ was a reasonable probe to detect sequences closely approximating the C9 sequence.

The CDR3 segments of the α and β chains of the TCR (VJα and VDJβ) are produced by apparently random recombination of the 3' ends of the Vα and Vβ genes with the 5' ends of Jα and DJβ genes respectively. Randomness is further enhanced by N insertions, nucleotides not directed by genetic templates (16). The practically unlimited potential variability of the CDR3 segments creates the diversity of the T cell repertoire; so it is fitting that the CDR3 segments, according to some models of the TCR structure, make contact with the peptide epitopes presented in the clefts of the MHC molecules (17). The CDR3 segments also define the most individual characteristic of a T cell clone. Thus the CDR3 segments constitute a clone's idiotope(s) as well as its private utensil for recognition of the target epitope. The CDR3 segments determine both how the clone sees antigen and how it can be seen as an individual cell.

Shared VDJ Motifs in General

The C9 VDJβ segment seems to be prominent and shared among individual NOD mice. It was detected in the thymus, spleen and islet infiltrates of different NOD mice as well as in the anti-p277 T cell clones and lines. In contrast, the C9 VJα sequence was not as abundant, and was undetectable in T cells sampled from the thymuses, spleens, or islet infiltrates. The importance of the C9 VDJβ was also suggested by the finding that anti-p277 T cells in the C57BL/6 mouse included clones with VDJβ regions similar by PCR and sequencing analysis to that of C9, despite the fact that the C57BL/6 clones used different Vβ genes (Vβ6, 8, 16) than did the NOD mice Vβ12. The presence of C9-like VDJβ segments among the C57BL/6 anti-p277 T cells is also noteworthy because the C57BL/6 and NOD mice have different H-2 alleles, although they share $D^b$ (1). The presence of one VDJβ motif associated with different MHC genes has a precedent in a motif common to Lewis rat T cells specific for myelin basic protein and to some T cells from humans suffering from multiple sclerosis (18). Although the antigenic specificity of the human T cells was not known, on the basis of the common VDJβ motif it was suggested that the epitope might be myelin basic protein.

Human Expression of C9 VDJ Motif

Our detection of the C9 VDJβ-like segment in different NOD, C57BL/6 and BALB/c mice suggests the existence of a common VDJ motif. Indeed, the independently isolated NOD clone, designated 41-E.2, was reported (15), like C9, to use Vβ12 and Jβ2.5 and had a VDJ region (SRLGNQDTQY (SEQ ID NO:12)) remarkably similar to that of C9 which differs in the VDJ region by an S in place of the R and an additional G: (SSLGNQDTQY (residues 48–58 of SEQ ID NO:1); the differences are underlined). Clone 4-1-E.2 was shown to adoptively transfer insulitis in non-diabetic 1-E+ transgenic NOD mice (15). The 4-1-B.2 clone was found to proliferate in the presence of islets, but there was no report of the antigen recognized by this clone. Interestingly, Durinovic-Bello and her colleagues reported the isolation of a T cell clone (K2.12) from a diabetic human with a TCR VDJ motif of SRLGNQ (residues 2–7 of SEQ ID NO:3) (see abstract, 21). For the C9 VDJβ motif to be detectable in so many instances would seem to require amplification of the clones bearing the motif. Such amplification could be attributed to positive selection; once the C9 VDJβ-like recombination occurs by chance, the clone bearing that VDJβ is driven to proliferation. Indeed, the C9 VDJβ marker was first detectable in the thymus and only later in the periphery and, finally in islets of NOD mice, during insulitis. Male NOD mice with accelerated insulitis and diabetes were also found to have the C9 VDJβ marker in their islets (not shown). Early positive selection of the C9 VDJ motif is supported by its relatively small content of N insertion nucleotides (19), probably only the three tta nucleotides encoding the L amino acid (see Table 1

The C9 VDJ Motif Can be Functional and Can Regulate IDDM

Irrespective of what mechanisms might positively select C9-like clones in the thymus, it is clear that anti-C9 anti-idiotypic T cells can regulate the activity of diabetogenic C9-like clones in the periphery: T cell vaccination with C9 leads to down-regulation of anti-p277 reactivity and prevents the development of diabetes in NOD mice (3). Moreover, immunization of NOD mice to the C9 VDJ peptide itself induces resistance to the development of diabetes (see below). The presence of the C9 VDJβ idiotope in individual NOD mice can explain how T cell vaccination with the C9 clone was able successfully to treat almost all NOD mice (3).

According to the present invention, it is shown that anti-idiotypic T cells specific to the C9 VDJ idiotype regulate IDDM in NOD mice: anti-idiotypic T cell reactivity is present in prediabetic NOD mice and falls spontaneously as the diabetogenic process develops; T cell vaccination against C9 activates the anti-idiotypic activity and prevents IDDM; anti-idiotypic T cell lines can adoptively transfer resistance to IDDM; and vaccination with the idiotypic VDJ peptide boosts the anti-idiotypic T cell reactivity and induces resistance to IDDM. The anti-idiotypic T cells can respond to the VDJ idiotope presented on intact C9 T cells without any added antigen presenting cells. These observations demonstrate the natural existence of anti-idiotypic T cells, their target TCR epitope, and their role in controlling autoimmune diabetes. The expression of disease seems to depend on the balance between diabetogenic T cells and regulatory anti-C9 VDJ anti-idiotypic T cells.

Proof of a Spontaneous Anti-idiotypic Network

NOD mice in our colony develop insulitis beginning at about 1 month of age. The female mice all progress to frank diabetes by 4 months of age. In contrast, only about 50% of the male mice develop clinical diabetes and do so by 6 months of age. We therefore studied female and male NOD mice for their T cell responses to hsp60, the target self antigen, and to C9, the prototype anti-hsp60 T cell. FIG. 4 shows the T cell proliferative responses of spleen cells taken for female and male NOD mice at various ages. Four week old female mice (FIG. 1, upper panel), at the onset of detectable insulitis, showed no T cell reactivity to hsp60 but did react to C9. With age, the spontaneous anti-idiotypic reactivity to C9 fell while the C9-like reactivity to hsp60 rose. After the onset of clinical diabetes, both types of T cell reactivity disappeared.

In the male mice (FIG. 4, lower panel), the anti-C9 anti-idiotypic reactivity declined later than it did in the more susceptible females. The C9-like anti-hsp60 reactivity also rose later. With time, the anti-idiotypic reactivity fell, but did not disappear, and the anti-hsp60 reactivity remained at a modest level as about half of the male mice remained free of diabetes. These results in untreated NOD mice suggested that the development of autoimmune diabetes is negatively associated with anti-C9 anti-idiotypic T cells and positively associated with anti-hsp60 (C9 like) T cells.

Proof that the VDJ Sequence is the C9 Idiotype

FIG. 5 demonstrated that the idiotypic peptide of C9 recognized by the anti-C9 T cells is the VDJ peptide of the TCR beta chain. Three month old female NOD mice were or were not vaccinated with irradiated C9 T cells and then tested their T cell proliferation to various NOD stimulator T cells and VDJ peptides: C9, N4 or anti-ovalbumin (anti-OVA). The N4 clone, which cannot mediate diabetes or vaccinate against it, was isolated along with C9 from prediabetic NOD mice (3). N4 reacts to Mycobacterial hsp65 but not significantly to human or to mouse hsp60 or to the p277 peptide of hsp60. We found earlier that N4 and C9 differ by 3 nucleic acids (2 amino acids) in the β chain VDJ region and that the anti-OVA T line expresses completely unrelated TCR α and β chains (Table 1). The prediabetic NOD mice showed T cell proliferative reactivity to the C9 clone and to the C9 VDJ peptide whether they were vaccinated with control T cells or were unvaccinated (FIG. 5, upper panel). Following vaccination with C9, there was a significant boost in the response to C9 and to the C9 VDJ peptide. There was no response to N4 or to N4 VDJ peptide, or to anti-OVA (FIG. 5, upper panel).

To confirm the equivalence of the responses to intact C9 cells and to its VDJ peptide, we vaccinated NOD mice with the C9 VDJ segment genetically engineered to be expressed within flagellin and tested the T cell responses to the T cells and peptides we used above. FIG. 5, lower panel, shows that the C9 VDJ construct boosted the specific response to intact C9 cells as well as to the C9 VDJ peptide. FIG. 6 shows that the T cell response to the C9 VDJ peptide may be boosted when the peptide is conjugated to the ovalbumin carrier (OVA) as well as to the C9 VDJ—flagellin construct. Therefore, various carrier molecules can be used to induce anti-idiotypic responses.

Also note that BALB\c mice, as well as NOD mice, can respond to C9 VDJ-conjugates (FIG. 6). Thus, the response to the C9 VDJ idiotype is not restricted to the NOD mice. Accordingly, it appears that the VDJ peptide of the TCR β chain constitutes the immunologic identity of C9 seen by the anti-idiotypic T cells.

Treatment of IDDM: By Anti-idiotypic T Cells and by the VDJ Peptide

FIG. 7 shows that anti-C9 anti-idiotypic T cells can protect against spontaneous diabetes. Adoptive transfer of anti-C9 T cells (FIG. 7, upper panel) and active vaccination with the C9 VDJ construct (FIG. 7, lower panel) were both effective in inhibiting disease.

T Cell Presents VDJ Idiotope

The C9 T cell presents its own TCR peptide to anti-C9 T cells directly. In the experiment shown in FIG. 8, anti-C9 T cells were separated from APC and purified C9 T cells, also free of APC. Both the C9 T cells and the anti-C9 anti-idiotypic T cell populations appeared functionally free of standard APC activity: these cells could not present OVA to the anti-OVA T cells. However, the C9 cells were found to stimulate the anti-idiotypic anti-C9 T cells. Indeed, addition of APC to the T cell cultures did not enhance, but actually seemed to decrease the T cell interaction. Thus, it appears that anti-C9 T cells recognize the C9 β chain VDJ epitope presented by C9 itself.

VDJ Idiotope is Associated with MHC

To test the major histocompatibility complex (MHC) element used by C9 in presenting its TCR peptide to the anti-idiotypic T cells, we used monoclonal antibodies to block the anti-C9 response. Table 3 shows the results of boosting the anti-C9 response with intact C9 cells. The bulk of the response to intact C9 or to the C9 VDJ on APC was blocked by antibodies specific for the $K^d$ MHC molecule. Anti IA antibodies also blocked the response, but to a lesser degree. There was no inhibition by antibodies to the $D^b$ molecule, although both the Kd and Db molecules are expressed in NOD. Thus, the anti-C9 anti-idiotypic T cell reactivity appeared to be both MHC class I-restricted to the K element and MHC class II restricted. The finding of both class I and class II restriction is compatible with the observation of both CD4 and CD8 anti-idiotypic T cells following T-cell vaccination in EAE (6). CD4 T cells usually recognize their peptide epitopes in the clefts of MHC class II molecules and CD8 T cells usually recognize their peptide epitopes in the clefts of MHC class I molecules. Thus, the C9 VDJ peptide, or parts of it, would seem to be able to be associated with the $IA^{NOD}$ or the $K^d$ molecules, but not with the $D^b$ molecule.

Idiotypic Network Regulation

The results presented here clarify the phenomenon of T cell regulation of autoimmunity in a spontaneous disease by showing that anti-idiotypic T cells are present without artificial intervention, that the expression of disease is associated with changes in the balance between the idiotypic T cells and the anti-idiotypic T cells, that the idiotypic peptide is the VDJ segment of the TCR chain, and that the idiotypic T cell presents its own idiotope to the regulatory anti-idiotypic T cells (20). Thus, a network exists that seems to connect the hsp60 p277 epitope to the shared TCR idiotypic peptide of C9, and, in turn, to the anti-idiotypic regulatory population. The spontaneous anti-idiotypic network seems to be particularly functional in the NOD mouse model of type I diabetes.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

TABLE 1

| | | | VDJ Region Sequence | | | | |
|---|---|---|---|---|---|---|---|
| Mouse | clone | Vβ V | N and D | | J | Jβ | SEQ ID NO |
| NOD | C9 | 12 A S S<br>gcc agc agt | L G<br>tta ggg | G<br>ggt | N Q D-<br>aac caa gac | 2.5 | 1 (res. 47–55)<br>6 |
| NOD | N4 | 11 A S S<br>gca aga agc | L W<br>tta tgg | T<br>gac | N Q D-<br>aac cca gac | 2.5 | 2 (res. 1–9)<br>13 |

TABLE 1-continued

| Mouse | clone | Vβ | V | | | N and D | | | J | | | Jβ | SEQ ID NO |
|---|---|---|---|---|---|---|---|---|---|---|---|---|---|
| | | | | | | VDJ Region Sequence | | | | | | | |
| NOD | 4-1-E.2 | 12 | A<br>gcc | S<br>agc | | R<br>aga | L<br>ctg | G<br>gga | | N<br>aac | Q<br>caa | D-<br>gac | 2.5<br>14 | 3 |
| C57BL/G | B2.1 | 6 | A<br>gcc | S<br>agc | S<br>agt | L<br>ctc | G<br>cga | L<br>ctg | G<br>ggg | A<br>gct | N<br>aac | Q<br>caa | D-<br>gac | 2.5<br>15 | 4 |

TABLE 2

Tissue distribution of C9 VDJ and VJ in NOD mice

| Age | probe | Female | | | Male | | |
|---|---|---|---|---|---|---|---|
| (months) | | thymus | spleen | islets | thymus | spleen | islets |
| 0.5 | α | – | – | nd | – | – | nd |
| | β | + | – | nd | + | – | nd |
| 1 | α | – | – | – | – | – | – |
| | β | + | + | + | + | + | – |
| 2 | α | – | – | – | – | – | – |
| | β | + | – | – | + | + | + |
| 3 | α | – | – | nd | – | – | nd |
| | β | + | + | nd | + | + | nd |
| 4 | α | – | – | nd | nd | nd | nd |
| | β | + | + | nd | nd | nd | nd |

TABLE 3

Anti-idiotypic anti-C9 responses are both MHC class I and class II restricted

| Immunization (in vivo) | Stimulator (in vitro) | Blocking antibody (2 mM) | Proliferative response (SI) | Inhibition (%) |
|---|---|---|---|---|
| C9 clone: $5 \times 10^6$ | irradiated C9 | none | 6.3 | — |
| C9 clone $5 \times 10^6$ | " | anti I-A | 4.8 | 28 |
| C9 clone $5 \times 10^6$ | " | anti $K^d$ | 2.5 | 72 |
| C9 clone $5 \times 10^6$ | " | anti $D^b$ | 6.5 | 0 |
| C9 clone $5 \times 10^6$ | C9 VDJ peptide | none | 7.0 | 0 |
| C9 clone $5 \times 10^6$ | " | anti I-A | 5.1 | 32 |
| C9 clone $5 \times 10^6$ | " | anti $K^d$ | 2.8 | 70 |
| C9 clone $5 \times 10^6$ | " | anti $D^b$ | 6.9 | 2 |

REFERENCES

1. Kikutani, H. et al., "The murine autoimmune diabetes model: NOD and related strains", *Advances in Immunol.* 51:285–322 (1992).

2. Elias, D., et al., "Induction and therapy of autoimmune diabetes in the non-obese-diabetic (NOD/Lt) mouse by a 65-kDa heatshock protein", *Proc Natl Acad Sci USA* 87:1576–1580 (1990).

3. Elias, D., et al. "Vaccination against autoimmune mouse diabetes with a T-cell epitope of human 65-kDa heatshock protein", *Proc. Natl. Acad. Sci. USA* 88:3088–3091 (1991).

4. Elias, D. et al., "Peptide therapy for diabetes in NOD mice", *Lancet* 343:704 (1994).

5. Elias, D., et al., "Induction of diabetes in standard mice by immunization to the n277 peptide of hsp60", Accompanying paper (1994).

6. Lider, O., et al., "Anti-idiotypic network induced by T cell vaccination against experimental autoimmune encephalomyelitis", *Science* 239:181 (1988).

7. Zhang, J., et al., "MHC-restricted depletion of human myelin basic protein-reactive T cells by T cell vaccination", *Science* 261:1451 (1993).

8. Bauminger, S., et al., "The use of carbodiimides in the preparation of immunizing conjugates", *Methods Enzymol.* 70:151 (1980).

9. Gotoh, M., et al., "Reproducible high yield of rat islets by stationary in vitro digestion following pancreatic ductal or portal venous collagenase digestion", *Transplantation* 43:725–30 (1987).

10. Scahfer, R., et al., "Optimizing oligonucleotide probes for DNA fingerprinting", *Electrophoresia* 9:369 (1988).

11. Casanova, J.-L., et al., "Optimal conditions for directly sequencing double-stranded PCR products with Sequenase", *Nucl. Acids Res.* 18:4028 (1990).

12. Acha-Orbea, H., et al., "Limited heterogeneity of T cell receptors from lymphocytes mediating autoimmune encephalomyelitis allows specific immune intervention", *Cell* 54:263–273 (1988).

13. Sherman, D. H., et al., "Molecular analysis of antigen recognition by insulin-specific T-cell hybridomas from B6 wild-type and bm12 mutant mice", *Mol and Cell Biol* 7:1865 (1987).

14. Koop, B. F., et al., "Organization, structure and function of 95 kb of DNA spanning the murine T-cell receptor Ca/CS region", *Genetics* 13:1209 (1992).

15. Nakano, N., et al., "T cell receptor V gene usage of islet β cell-reactive T cells is not restricted in non-obese diabetic mice", *J Exp Med* 173:1091 (1991).

16. Epplen, J. T., et al., "Mammalian T-lymphocyte antigen receptor genes: genetic and nongenetic potential to generate variability", *Hum. Genet.* 75:300–310 (1987).

17. Chothia, C., et al., "The outline structure of the T-cell ab receptor", *The EMBO J* 7:3745–3755 (1988).

18. Oksenberg, R. J., et al., "Selection for T-cell receptor Vβ-Dβ-Jβ gene rearrangements with specificity for a myelin basic protein peptide in brain lesions of multiple sclerosis", *Nature* 362:68–70 (1993).

19. Engler, P., et al., "N region diversity of a transgenic substrate in fetal and adult lymphoid cells", *J Exp Med* 176:1399 (1992).

20. Cohen, I. R, "The cognitive paradigm and the immunological homunculus", *Immunol Today* 13:490 (1992).

21. Durinovic-Bello, I., et al., "HLA-DQ-restricted, Islet-specific T Cell Clones of a Type I diabetic Patient: T Cell Receptor Sequence Similarities to Insulitis-inducing T Cells of Nonobese Diabetic (NOD) Mice", 13th International Immunology and Diabetes Workshop (1994).

22. Durinovic-Bello, I., et al., "HLA-DQ-restricted, Islet-specific T Cell Clones of a Type I diabetic Patient: T Cell Receptor Sequence Similarities to Insulitis-inducing T Cells of Nonobese Diabetic (NOD) Mice", *Diabetes*, 43:1318–1325 (Nov. 1994).

23. Castano et al., "Type-I Diabetes: A Chronic Autoimmune Disease of Human, Mouse, and Rat", *Annu. Rev. Immunol.*, 8:647–679 (1990).

24. Bowman et al., "Prevention of Diabetes in the NOD Mouse: Implications for Therapeutic Intervention in Human Disease", *Immunol. Today*, 15(3):115–120 (1994).

25. Williams, G., "IDDM: Long Honeymoon, Sweet Ending", *Lancet*, 343:684–685 (1994).

26. Bendelac et al., "Syngeneic Transfer of Autoimmune Diabetes from Diabetic NOD Mice to Healthy Neonates: Requirement for both L3T4+ and Ly+–2+ T Cells", *J. Exp. Med.*, 166:823–832 (1987).

27. Elias, D., "The NOD Mouse: A Model for Autoimmune Insulin-Dependent Diabetes", *Autoimmune Disease Models. A Guidebook*, pp. 147–161 (1994).

28. Kaufman et al., "Spontaneous Loss of T-cell Tolerance to Glutamic Acid Decarboxylase in Murine Insulin-Dependent Diabetes", *Nature*, 366:69–72 (1993).

29. Tisch et al., "Immune Response to Glutamic Acid Decarboxylase Correlates with Insulitis in Non-Obese Diabetic Mice", *Nature*, 366:72–75 (1993).

30. Howell et al., "Vaccination against Experimental Allergic Encephalomyelitis with T Cell Receptor Peptides", *Science*, 246:668–670 (1989) [erratum at *Science*, 247:1167 (1990)].

31. Vandenbark et al., "Immunization with a Synthetic T-Cell Receptor V-Region Peptide Protects against Experimental Autoimmune Encephalomyelitis", *Nature*, 341:541–544 (1989).

32. Behlke et al., "Alternative Splicing of Murine T-cell Receptor β-Chain Transcripts", *Nature*, 322:379–382 (1984).

33. Mallssen et al., "Mouse T Cell Antigen Receptor: Structure and Organization of Constant and Joining Gene Segments Encoding the β Polypeptide", *Cell*, 37:1101–1110 (1984).

We claim:

1. A peptide consisting of an amino acid sequence of about 7–24 amino acid residues in length, said amino acid sequence comprising a "VDJ" region, obtained from the CDR3 of the β chain of a T cell receptor reactive with heat shock protein 60 (hsp60), having the formula

V-D-J, which is capable of activating anti-idiotypic T cells that recognize and down-regulate autoimmune anti-hsp60 T cells, and in which "V" includes the dipeptide sequence A-S, "D", preferably having 2–5 amino acid residues, includes the dipeptide sequence L-G, and "J" includes the tripeptide sequence N-Q-D, or a salt, variant or chemical derivative of said amino acid sequence of the peptide, said chemical derivative being a peptide in which chemical moieties are formed on the functional groups of amino acid side chains and said variant being a peptide in which one or more amino acid residues are deleted, added or replaced with other amino acid residues, wherein said salt, variant and chemical derivative all have the ability to immunologically cross-react with the VDJ region of a T cell receptor β chain such that T cells, which recognize and down-regulate autoimmune anti-hsp60 T cells, are capable of being activated thereby and said variant retains the dipeptide sequence A-S in "V", the dipeptide sequence L-G in "D", and the tripeptide sequence N-Q-D in "J".

2. The peptide of claim 1 in which "V" includes the tripeptide sequence A-S-S.

3. The peptide of claim 1 in which "D" includes the tripeptide sequence L-G-G, the tripeptide sequence R-L-G or the pentapeptide sequence L-G-L-G-A (residues 4–8 of SEQ ID NO:4).

4. The peptide of any of claim 1, wherein the dipeptide sequence A-S of "V" is part of the tripeptide adjacent to "D".

5. The peptide of any of claim 1, wherein the tripeptide sequence N-Q-D of "J" is adjacent to "D".

6. The peptide of any of claim 1, wherein "V" comprises a "Vβ" segment which segment includes at least a portion of the C-terminal end of a protein encoded by a Vβ gene.

7. The peptide of claim 6, wherein the C-terminal tripeptide sequence of said Vβ segment includes the dipeptide sequence A-S.

8. The peptide of claim 6 in which said segment includes from 1 to about 10 amino acid residues of the C-terminal end of the protein encoded by the Vβ gene.

9. The peptide of claim 6, in which said Vβ gene is selected from the group consisting of Vβ6, Vβ8, Vβ12, and Vβ16.

10. The peptide of any claim 1, wherein "J" comprises a "Jβ" segment which segment includes at least a portion of the N-terminal end of a portion encoded by a Jβ gene.

11. The peptide of claim 10, wherein the N-terminal tripeptide sequence of said Jβ segment is N-Q-D.

12. The peptide of claim 10 in which said segment includes from 1 to about 10 amino acid residues of the N-terminal end of the protein encoded by the Jβ gene.

13. The peptide of claim 10 in which said Jβ gene is Jβ2.5.

14. A peptide in accordance with claim 1 having up to about 24 amino acid residues comprising the sequence A-S-S-L-G-G-N-Q-D (residues 47–55 of SEQ ID NO:1).

15. A peptide in accordance with claim 1 having up to about 24 amino acid residues comprising the sequence A-S-R-L-G-N-Q-D (SEQ ID NO:3).

16. A peptide in accordance with claim 1 having up to about 24 amino acid residues comprising the sequence A-S-S-L-G-L-G-A-N-Q-D (SEQ ID NO:4).

17. A peptide in accordance with claim 1 having up to about 24 amino acid residues comprising the sequence A-S-S-L-G-A-N-Q-D (SEQ ID NO:16).

18. A peptide in accordance with claim 1 consisting of 7 to 24 amino acid residues, comprising a "VDJ" region of the formula

V-D-J in which "V" includes the dipeptide sequence Ala-Ser immediately adjacent to "D" or separated from "D" by one amino acid residue, "D" has 2–5 amino acid residues, among which is the dipeptide sequence Leu-Gly, and "J" includes the tripeptide sequence Asn-Gln-Asp immediately adjacent to "D".

19. The peptide in accordance with claim 1, wherein said "VDJ" region is obtained from the CDR3 of the β chain of a T cell receptor reactive with the peptide p277 of hsp60 and wherein said anti-idiotypic T cells which are capable of being activated by the peptide, recognize and down-regulate autoimmune anti-hsp60 T cells which are autoimmune anti-p277 T cells.

20. An agent for detecting the presence of anti-idiotypic T cells involved in the recognition of anti-p277 T cells consisting of a peptide of claim 1 conjugated to or within an exogenous polypeptide carrier.

21. A conjugate consisting of the peptide of claim 1 conjugated to a second molecule.

22. The conjugate of claim 21 in which said second molecule is a detectable label.

23. The conjugate of claim 21 in which the second molecule is a polypeptide.

24. The conjugate of claim 21 in which the second molecule is a small organic molecule.

25. A pharmaceutical composition comprising a peptide of claim 1.

26. The pharmaceutical composition of claim 25 which is a vaccine.

27. A method of modulating anti-idiotypic T cell activity in an individual, said activity associated with the ability of anti-idiotypic T cell to recognize anti-p277 T cells, comprising administering to the individual an amount of a peptide in accordance with claim 1 effective to regulate the activity of said anti-idiotypic T cells.

28. The method of claim 27 in which said activity is potentiated.

29. A method for the prevention and treatment of insulin-dependent diabetes mellitus comprising activating autologous T cells against a peptide in accordance with claim 1 and re-administering them to a patient.

30. A method for the diagnosis or staging of IDDM or for monitoring the course of treatment of IDDM, comprising assaying the T cells of the serum of the subject being tested for proliferation or cytokine production upon in vitro contact with a peptide in accordance with claim 1.

31. A DNA construct comprising a polynucleotide sequence encoding the peptide of claim 1, or its complement.

32. An oligonucleotide comprising a polynucleotide sequence complementary to at least a portion of a DNA sequence encoding a peptide of claim 1.

\* \* \* \* \*